(12) United States Patent
Getts et al.

(10) Patent No.: US 11,484,506 B2
(45) Date of Patent: Nov. 1, 2022

(54) PROCESS FOR THE PREPARATION OF TOLERIZING IMMUNE-MODULATING PARTICLES

(71) Applicant: COUR PHARMACEUTICALS DEVELOPMENT COMPANY, INC., Northbrook, IL (US)

(72) Inventors: Daniel R. Getts, Northbrook, IL (US); Frank Fokta, Northbrook, IL (US); Ryan Pearson, Northbrook, IL (US)

(73) Assignee: COUR PHARMACEUTICALS DEVELOPMENT COMPANY, INC., Northbrook, IL (US)

(*) Notice: Subject to any disclaimer, the term of this patent is extended or adjusted under 35 U.S.C. 154(b) by 208 days.

(21) Appl. No.: 15/999,871

(22) PCT Filed: Feb. 21, 2017

(86) PCT No.: PCT/US2017/018743
§ 371 (c)(1),
(2) Date: Aug. 20, 2018

(87) PCT Pub. No.: WO2017/143346
PCT Pub. Date: Aug. 24, 2017

(65) Prior Publication Data
US 2021/0290558 A1 Sep. 23, 2021

Related U.S. Application Data

(60) Provisional application No. 62/296,840, filed on Feb. 18, 2016.

(51) Int. Cl.
*A61K 9/51* (2006.01)
*A61K 47/26* (2006.01)

(52) U.S. Cl.
CPC .......... *A61K 9/5153* (2013.01); *A61K 9/5192* (2013.01); *A61K 47/26* (2013.01)

(58) Field of Classification Search
None
See application file for complete search history.

(56) References Cited

U.S. PATENT DOCUMENTS 4,574,058 A 3/1986 Baschang et al.
2011/0293644 A1 12/2011 Anderson et al.
(Continued)

FOREIGN PATENT DOCUMENTS

WO 2014089160 A1 6/2014
WO WO-2014/160465 A2 10/2014
(Continued)

OTHER PUBLICATIONS

Kim (Production of composites by using gliadin as a bonding material, Journal of Cereal Science, vol. 54, 2011, pp. 168-172). (Year: 2011).*

(Continued)

*Primary Examiner* — Melissa S Mercier
(74) *Attorney, Agent, or Firm* — Honigman LLP; Lucy X. Yang; Jonathan P. O'Brien

(57) ABSTRACT

The present disclosure is directed to a method of preparing a pharmaceutical composition comprising tolerizing immune-modulating particles of polymer-encapsulated gliadin.

27 Claims, 10 Drawing Sheets

Single Emulsion Process

(56) References Cited

U.S. PATENT DOCUMENTS

2015/0010631 A1* 1/2015 Getts .................. A61P 3/10
424/489
2015/0297531 A1* 10/2015 Ensign ............... A61K 9/5146
424/497

FOREIGN PATENT DOCUMENTS

WO    WO-2014/169255 A1    10/2014
WO    WO-2015/023796 A2    2/2015

OTHER PUBLICATIONS

Jung et al. (Cardiovascular Protective Properties of KiwiFruit Extracts in Vitro Biological and Pharmaceutical Bulletin, vol. 28, No. 9, 2005, p. 1782-1785). (Year: 2005).*
Arangoa et al., Research Note—Evaluation and Characterisation of Gliadin Nanoparticles and Isolates by Reversed-Phase HPLC, J. Cereal Sci., 31(2):223-8 (Mar. 2000).
Bible et al., Attachment of stem cells to scaffold particles for intra-cerebral transplantation, Nat. Protoc., 4(10):1440-53 (2009).
Bietz et al., Gliadin analysis by reversed-phase high-performance chromatography: Optimization of extraction conditions, Cereal Chem., 61(2):124-129 (1984).
Bruchez et al., Semiconductor nanocrystals as fluorescent biological labels, Science, 281(5385):2013-6 (Sep. 1998).
Brus, A simple model for the ionization potential, electron affinity, and aqueous redoc potentials of small semiconductor crystallites, J. Chem. Phys., 79:5566 (1983).
Danhier et al., PLGA-based nanoparticles: an overview of biomedical applications, J. Control. Release, 161(2):505-22 (Jul. 2012).
Etienne et al., Third-order nonlinear optical properties of a cadmiun sulfide-dendrimer nanocomposite, Appl. Phys. Lett., 87:181913 (2005).
International Application No. PCT/US17/18743, International Search Report and Written Opinion, dated Apr. 25, 2017.
Jung et al., Cardiovascular protective properties of kiwifruit extracts in vitro, Biol. Pharm. Bull., 28(9):1782-5 (Sep. 2005).
Kim et al., Production of composites by using gliadin as a bonding material, J. Cereal Sci., 54(1):168-72 (Jul. 2011).
Lemon et al., Preparation and Characterization of Dendrimer-Encapsulated CdS Semiconductor Quantum Dots, J. Am. Chem. Soc., 122(51):12886-7 (2000).
Niemeyer, Functional hybrid devices of proteins and inorganic nanoparticles, Angew. Chem. Int. Ed. Engl., 42(47):5796-800 (2003).
Ribeiro et al., The Genetic Variability of Wheat Can Ensure Safe Products for Celiac Disease Patients?, Int. J. Celiac Dis., 2(1):24-6 (2014).
Waggoner et al., Covalent labeling of proteins and nucleic acids with fluorophores, Methods Enzymol., 246:362-73 (1995).

* cited by examiner

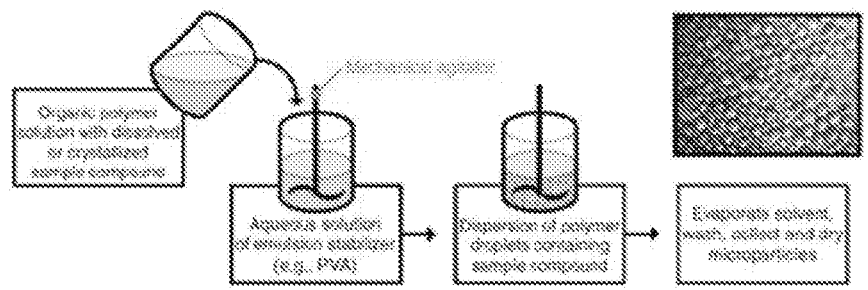
FIG. 1 Single Emulsion Process
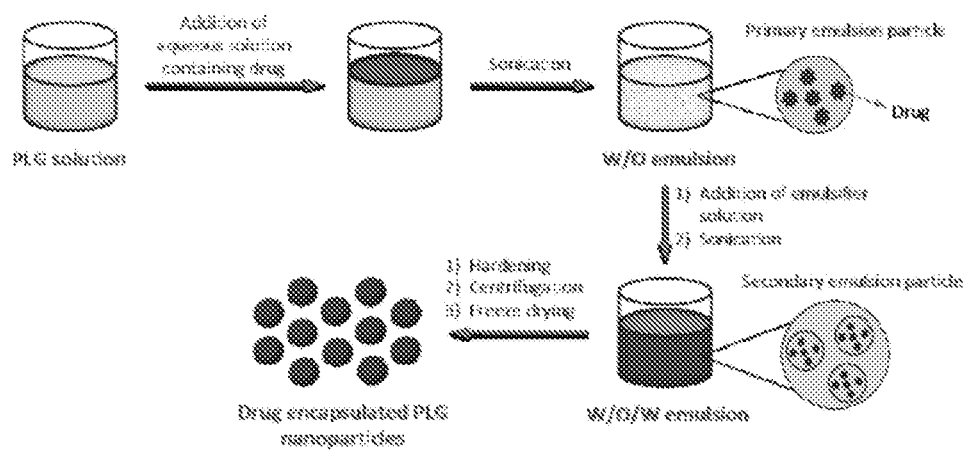
FIG. 2 Double Emulsion Process

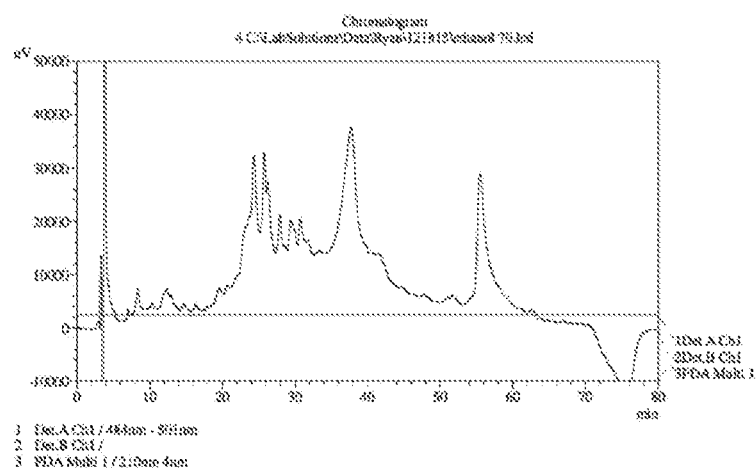
FIG. 3 Gliadin Reference RP-HPLC Chromatogram
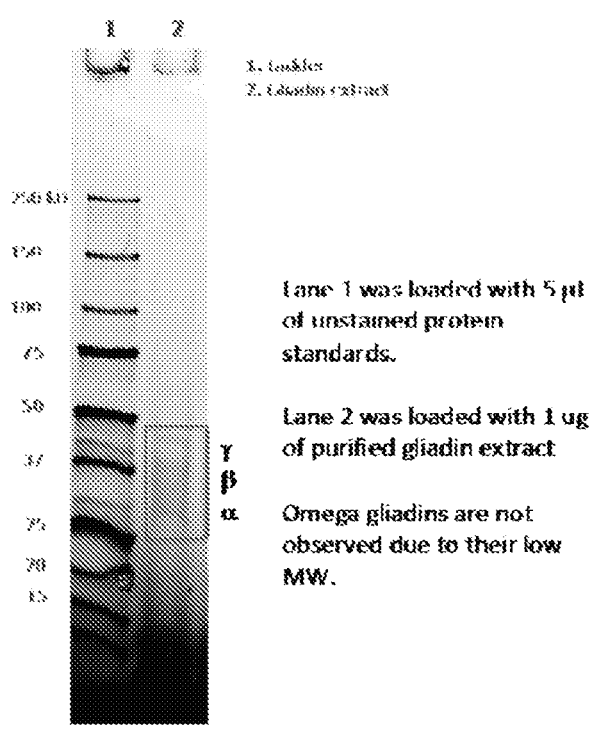
FIG. 4 Gliadin Reference SDS-PAGE gel FIGS. 5A-F. RP-HPLC chromatograms of 50, 60, and 70% ethanol, acetic acid, TFA and DMSO/TFA gliadin extracts obtained from Sigma.

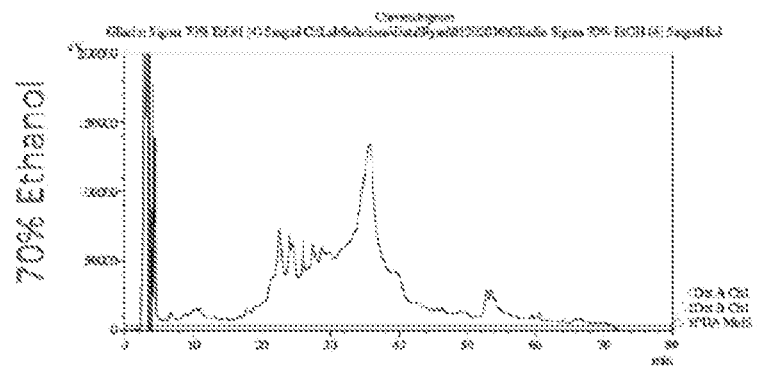
FIG. 6A (70% EtOH, Sigma)
FIG. 6B (Acetic Acid, Sigma)
FIG. 6C (70% EtOH, MP Biomedical)

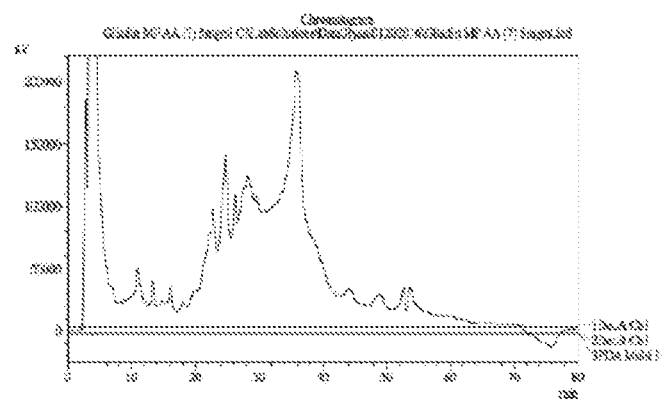
FIG. 6D (Acetic Acid, MP Biomedical)
FIGS. 6A-D HPLC chromatograms 70% ethanol and acetic acid gliadin extracts obtained from Sigma or MP Biomedical.

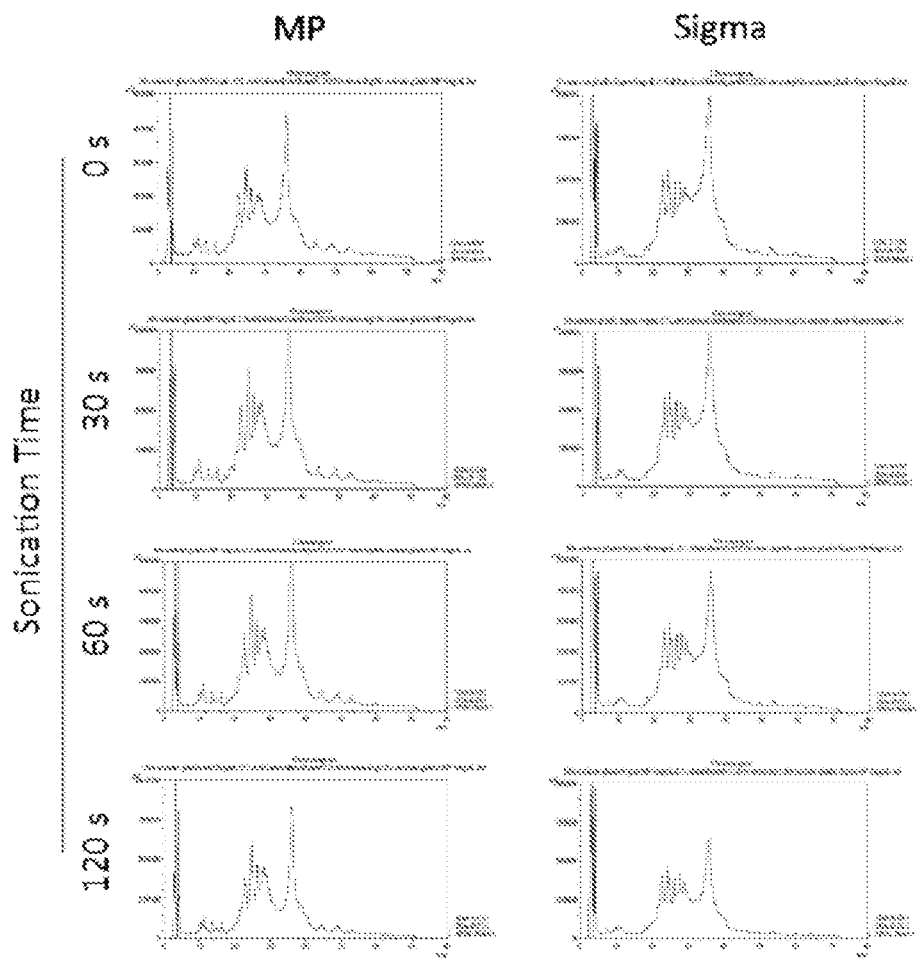
FIG. 7 - Effect of sonication time on HPLC chromatograms of 70% ethanol gliadin extracts obtained from Sigma-Aldrich or MP Biomedical.

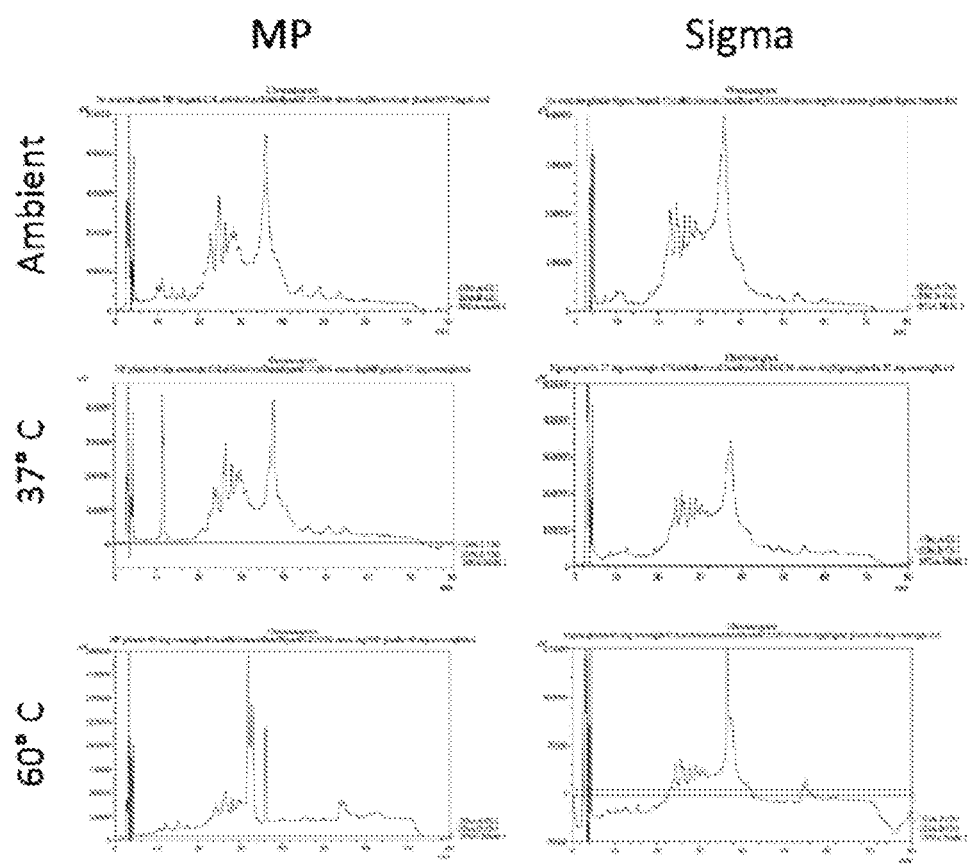
FIG. 8 - Effect of overnight incubation at the indicated temperatures on HPLC chromatograms of 70% ethanol gliadin extracts obtained from Sigma or MP Biomedical.

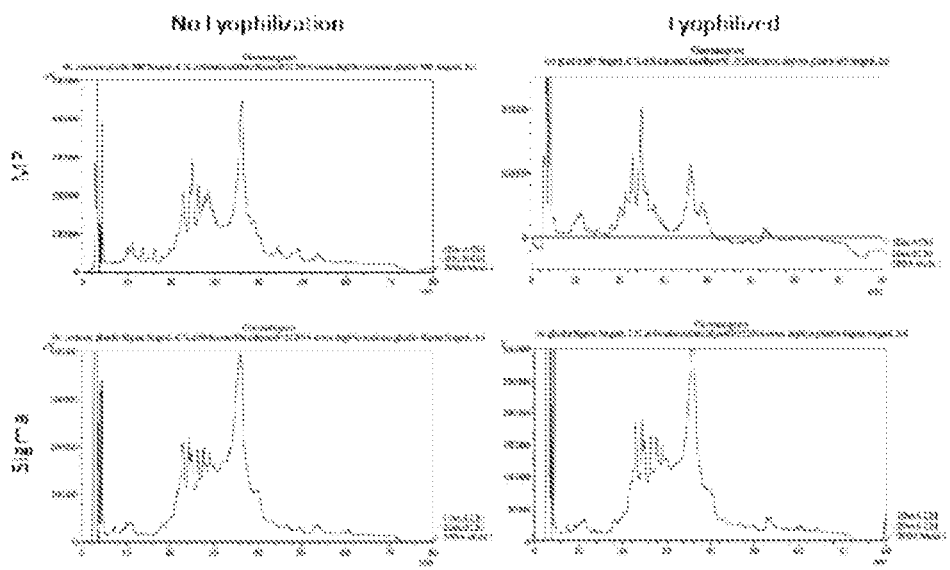
FIG. 9 - Comparison of the HPLC chromatograms of 70% ethanol extracted gliadin versus 70% ethanol extracted and lyophilized gliadin.
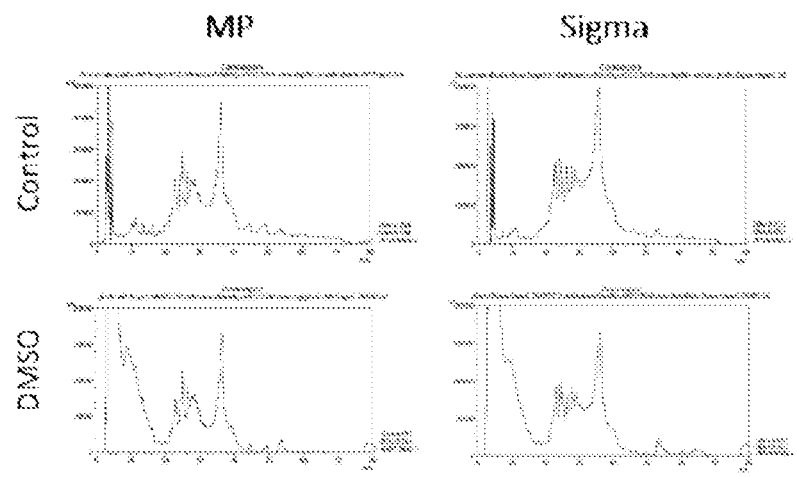
FIG. 10 - HPLC chromatograms of 70% ethanol gliadin extracts obtained from Sigma or MP Biomedical mixed with DMSO.

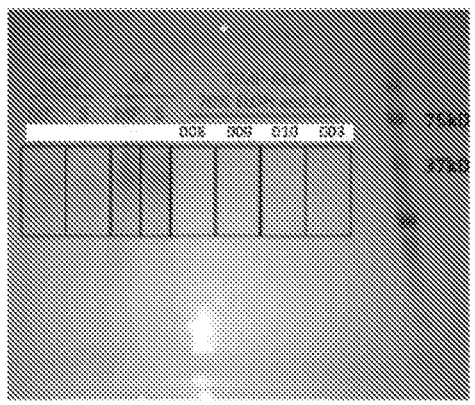
FIG. 11 - SDS-PAGE comparing MP Biomedical and Sigma crude gliadin extracts from 70% ethanol and acetic acid (AA) and TIMP-GLIA008, TIMP-GLIA009, TIMP-GLIA010, and TIMP-GLIA003.
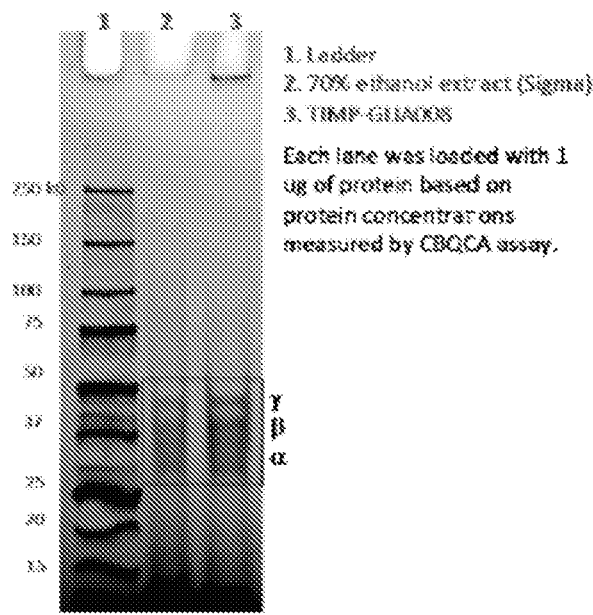
FIG. 12 - SDS-PAGE analysis of 70% ethanol gliadin extract and TIMP-GLIA008 demonstrating successful encapsulation of gliadin proteins.

PROCESS FOR THE PREPARATION OF TOLERIZING IMMUNE-MODULATING PARTICLES

CROSS REFERENCE TO RELATED APPLICATIONS

This application claims the benefit of U.S. Provisional Application No. 62/296,840, filed Feb. 18, 2016, the contents of which is incorporated herein by reference in its entirety.

BACKGROUND

Celiac (coeliac) disease (CD) is an autoimmune disorder that can occur in genetically predisposed people where the ingestion of gluten leads to damage in the small intestine. It is estimated to affect 1 in 100 people worldwide. It has been estimated that two and one-half million Americans remain undiagnosed and are at risk for long-term health complications. There are no approved drugs on the market to treat celiac patients and long-term the disease pre-disposes patients to a number of other disorders including infertility, reduced bone density, neurological disorders, some cancers, and other autoimmune diseases.

Celiac disease is caused by an abnormal intestinal T-cell response to gliadin, a prolamin (gluten protein) found in wheat, and similar proteins found in the crops of other grains such as barley and rye. Upon exposure to gliadin, the enzyme tissue transglutaminase modifies the protein, and the immune system cross-reacts with the small-bowel tissue, causing an inflammatory reaction. Current treatment options often involve nonspecific immunosuppression.

SUMMARY

Targeted immune (antigen) tolerance is an alternative therapy for the treatment of a variety of autoimmune diseases that provides advantages over nonspecific immunosuppression treatments. Intravenous infusion of apoptotic syngeneic splenocytes linked with peptide or protein autoantigens using ethylene carbodiimide (ECDI) is an effective method for inducing peripheral, antigen-specific tolerance for treatment of autoimmune disease. Biodegradable poly (lactic-co-glycolic acid) (PLG) nanoparticles can function as a safe, cost-effective, and highly efficient alternative to cellular carriers for the induction of antigen-specific T cell tolerance. PLG particles with surfactant modifications surpass the efficacy of commercially available particles in their ability to couple peptides and/or peptide epitopes and to prevent disease induction.

Toleragenic Immune Modifying nanoParticles (TIMP) are poly(lactide-co-glycolide) particles that contain autoreactive protein or peptide epitopes. The identification of gliadins as the primary epitopes in celiac disease suggests that TIMP-containing gliadin (TIMP-GLIA) may serve as a tool to induce tolerance to gluten and potentially cure CD.

Therefore, it is important to develop a manufacturing process that provides therapeutically effective encapsulated gliadin.

Manufacturing processes typically involve numerous steps, any one of which could affect the performance properties of the resulting product. A major objective of developing TIMP-GLIA dosage forms for indications such as celiac disease and associated symptoms is to provide controlled delivery of the drug (e.g., antigen) at therapeutically effective concentrations over a desired period of time, thereby enhancing therapeutic efficacy, patient compliance, and reducing both side effects and cost of treatment.

The present disclosure, in various embodiments, is directed to methods of preparing pharmaceutical composition comprising TIMP-GLIA particles via a double emulsion solvent evaporation.

Some embodiments of the present disclosure are directed to a method for preparing a pharmaceutical composition comprising TIMP-GLIA particles, the method comprising: (a) homogenizing gliadin dissolved in an aqueous media with an oil phase including a polymer to produce water-in-oil primary emulsion particles; (b) mixing the primary emulsion particles with a surfactant; (c) homogenizing the mixture of (b) to provide secondary emulsion particles; and (d) hardening the secondary emulsion particles.

In certain embodiments, hardening the secondary emulsion particles includes evaporation of the oil phase. In some embodiments, the aqueous media is 70% ethanol. In some embodiments, gliadin concentration in the aqueous media is greater than about 25 mg/mL. In certain embodiments, the hardened secondary emulsion particles are free from trifluoroacetic acid. In some embodiments, the method is free from trifluoroacetic acid.

Some embodiments of the present disclosure are directed to a process for the preparation of a pharmaceutical composition comprising TIMP-GLIA particles, said process comprising the steps of: a) producing primary water-in-oil emulsion particles by homogenization of gliadin dissolved in an aqueous media in an oil phase comprising polymer; b) adding an emulsifier to the primary emulsion particles; and c) homogenizing the mixture of step b) to provide secondary water-in-oil-in-water emulsion particles.

In some embodiments, gliadin is purified by extraction from crude gliadin from wheat with an extraction solvent.

In some embodiments, the extraction solvent is 70% ethanol.

Some embodiments of the present disclosure are directed to the process further comprising the steps of: d) hardening the secondary emulsion particles; e) centrifuging the hardened secondary emulsion particles; and f) freeze drying the secondary emulsion particles.

In some embodiments, the polymer is a biodegradable polymer.

Unless otherwise defined, all technical and scientific terms used herein have the same meaning as commonly understood by one of ordinary skill in the art to which this disclosure pertains. In the case of conflict, the present specification, including definitions, will control. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents, and other references mentioned herein are incorporated by reference herein, for all purposes. The references cited herein are not admitted to be prior art to the claimed disclosure. In addition, the materials, methods, and examples are illustrative only and are not intended to be limiting.

Other features and advantages of the present disclosure will be apparent from the following detailed description and claims.

BRIEF DESCRIPTION OF THE DRAWINGS

FIG. 1 provides a schematic of single emulsion solvent evaporation method.

FIG. 2 provides a schematic of double emulsion solvent evaporation method.

FIG. 3 provides a gliadin reference chromatogram (RP-HPLC).

FIG. 4 provides a gliadin reference SDS-PAGE gel.

FIG. 6A-D provide HPLC chromatograms 70% ethanol and acetic acid gliadin extracts obtained from different sources.

FIG. 7 shows effect of sonication time on HPLC chromatograms of 70% ethanol gliadin extracts obtained from different sources.

FIG. 8 shows effect of overnight incubation at the indicated temperatures on HPLC chromatograms of 70% ethanol gliadin extracts obtained from different sources.

FIG. 9 provides comparison of the HPLC chromatograms of 70% ethanol extracted gliadin versus 70% ethanol extracted and lyophilized gliadin.

FIG. 10 provides HPLC chromatograms of 70% ethanol gliadin extracts obtained from different sources mixed with DMSO.

FIG. 11 provides SDS-PAGE gel comparing crude gliadin extracts from 70% ethanol and acetic acid (AA) and TIMP-GLIA008, TIMP-GLIA009, TIMP-GLIA010, and TIMP-GLIA003.

FIG. 12 shows SDS-PAGE gel analysis of 70% ethanol gliadin extract and TIMP-GLIA008 demonstrating encapsulation of gliadin proteins.

DETAILED DESCRIPTION

Figure 5A:
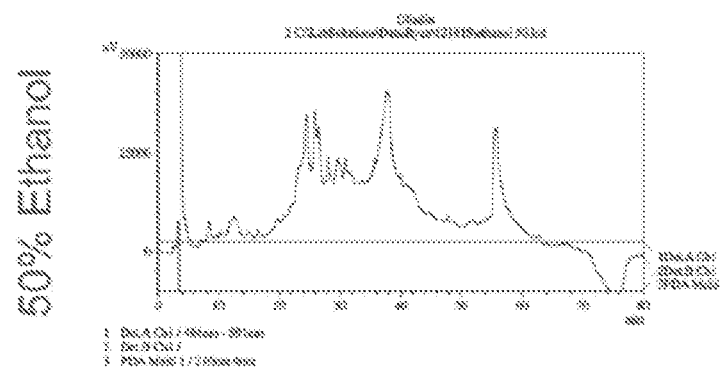
FIG. 5A-F provide RP-HPLC chromatograms of 50, 60, and 70% ethanol, acetic acid, TFA, and DMSO/TFA gliadin extracts.

The present disclosure is directed, in various embodiments, to preparation and characterization of biodegradable poly(lactide-co-glycolide) particles that have been surface-functionalized with a high density of carboxylate groups and contain soluble antigen (e.g., gliadin) within their cores that are surrounded by a shell of poly(lactide-co-glycolide) for tolerance induction in autoimmune disease and/or for the treatment of allergies.

In certain embodiments, a high density of carboxylate groups is achieved by the use of poly(ethylene-alt-maleic anhydride) (PEMA), a polymer with carboxylate groups incorporated into its backbone, as the surfactant for the emulsification process.

Certain embodiments of the present disclosure relate to a process of preparing TIMP-GLIA particles via a double emulsion solvent evaporation method. In some embodiments, the process of the present disclosure utilizes 50-70% ethanol extracts of gliadin and provides TIMP-GLIA particles with higher proportion of therapeutic gliadin proteins in the particle formulation.

The present disclosure details the formulation and partial characterization of biodegradable poly(lactide-co-glycolide) particles that have been surface-functionalized with a high density of carboxylate groups and contain soluble antigen within their cores that are surrounded by a shell of poly (lactide-co-glycolide) for tolerance induction in autoimmune disease and for the treatment of allergies.

"Antigen" as used herein refers to any moiety, for example, a peptide, that is recognized by the host's immune system. Examples of antigenic moieties include, but are not limited to, autoantigens and/or bacterial or viral proteins, peptides or components. Without being bound by theory, while the negatively charged beads themselves may be recognized by the immune system, the negatively charged beads with nothing more attached thereto are not considered an "antigenic" for the purposes of the disclosure.

"Epitope" as used herein is also known as "antigenic determinant", is the part of an antigen that is recognized by the immune system, specifically by antibodies, B cells, or T cells. For example, the epitope is the specific piece of the antigen that an antibody binds to. The part of an antibody that binds to the epitope is called a paratope. Although epitopes are usually non-self-proteins, sequences derived from the host that can be recognized (as in the case of autoimmune diseases) are also epitopes. T cell epitopes are presented on the surface of an antigen-presenting cell, where they are bound to MHC (major histocompatibility complex) molecules. In humans, professional antigen-presenting cells are specialized to present MHC class II peptides, whereas most nucleated somatic cells present MHC class I peptides. T cell epitopes presented by MHC class I molecules are typically peptides between 8 and 11 amino acids in length, whereas MHC class II molecules present longer peptides, 13-17 amino acids in length, and non-classical MHC molecules also present non-peptidic epitopes such as glycolipids.

In some embodiments, the antigen comprises an autoimmune antigen, an antigen expressed on a tissue to be transplanted into a subject, an enzyme, or an allergen. In one of the embodiments, the antigen comprises, for example, gliadin. In further embodiments, the particles are coupled to an antigen comprising one or more epitopes.

As used herein, a gliadin-associated particle refers to particle that has a covalent or non-covalent interaction with a celiac disease associated antigen. In certain embodiments, a gliadin-associated particle is a particle that is conjugated, linked, encapsulated, or adsorbed to gliadin. For example, TIMP-GLIA is a gliadin-associated particle.

Gliadins are mainly monomeric proteins with molecular weights (MWs) around 28,000-55,000 and can be classified according to their different primary structures into the alpha/beta-, gamma- and omega-type. Gliadens may also be extracted from Rye and Barley.

Gliadin for wheat (e.g., Sigma-Aldrich (Cat No. G3375) or MP Biomedical (Cat No. 0210177810)) can be used as crude gliadin. Gliadin source material can be isolated and tested as solute and as a lyophilized powder. Crude gliadin samples extracted with extraction solvent, e.g., ethanol and acetic acid, can be analyzed by the protein assay, RP-HPLC, SDS-PAGE, and mass spectrometry.

The epitopes from the α-gliadins are considered to have particularly high clinical relevance with regard to both the adaptive and innate response that leads to the development of celiac disease. A sub-fraction of α-gliadins, A-gliadins, may be particularly important due to its severe CD allergenicity. (Ribeiro, M. et al. International Journal of Celiac Disease, 2014, Vol. 2, No. 1, 24-26)

According to some embodiments, the gliadin epitopes are SEQ ID NOs: 13, 14, 16, 320, or 321, as described in U.S. Patent Application Publication No. 2011/0293644, hereby incorporated in its entirety for all purposes.

"Water-in-oil-in-water" (W/O/W) emulsion is an example of a double emulsion, in which dispersions of small water droplets within larger oil droplets are themselves dispersed in a continuous aqueous phase. Emulsions occur in many forms of processing and are used extensively by the foods, cosmetics and drug delivery. Because of their compartmentalized internal structure, double emulsions can provide advantages over simple oil-in-water emulsions for encapsulation, such as the ability to carry both polar and non-polar cargos (pharmaceutical/biological agent, e.g., proteins), and improved control over release of therapeutic molecules. The preparation of double emulsions typically requires surfactants or their mixtures for stability. The surfactants stabilize droplets subjected to extreme flow, leading to direct, mass production of robust double nanoemulsions that are amenable to nanostructured encapsulation applications in various industries.

"Homogenization" as used herein relates to an operation using a class of processing equipment referred to as homogenizers that are geared towards reducing the size of droplets in liquid-liquid dispersions. Factors that affect the particle or droplet size include but are not limited to the type of emulsifier, emulsifier concentration, solution conditions, and mechanical device (homogenizing power; pressure, rotation speed, time). Non-limiting examples of homogenizers include high speed blender, high pressure homogenizers, colloid mill, high shear dispersers, ultrasonic disruptor membrane homogenizers, and ultrasonicators. Mechanical homogenizers, manual homogenizers, sonicators, mixer mills, vortexers, and the like may be utilized for mechanical and physical disruption within the scope of the disclosure.

The present disclosure provides processes for the production of nanoparticle carriers for drug delivery, said nanoparticles being produced by preparing a double emulsion of water-oil-water including one or more polymers that form the basis of the nanoparticle carrier; blending the drug to be delivered into one or more of the emulsion phases; and freeze drying the emulsion to form nanoparticles of a narrow particle size distribution of about 400 nm to about 800 nm.

In certain embodiments, the average particle size of the emulsion particles are about 400 nm to about 800 nm. In certain embodiments, the average particle size of the emulsion particles are about 400, 500, 600, 700, or about 800 nm.

Preparation of nanoparticle via a double emulsion solvent evaporation method enables the encapsulation of proteins and other drug molecules within nanoparticles. The process comprises producing a water-in-oil-in-water (W/O/W) emulsion where the protein dissolved in an aqueous media is dispersed by homogenization (e.g., sonication or blending) in an oil phase containing polymer (primary emulsion). An emulsifier solution is then added to the primary emulsion followed by an additional round of homogenization (e.g., sonication or blending) to produce the W/O/W emulsion.

TIMP-GLIA particles can be prepared by a single emulsion solvent evaporation method (see, e.g., FIG. 1). Poly (lactide-co-glycolide) (PLGA) is used as the polymer to form the particles and proteins present in crude gliadin extract from wheat are used as the therapeutic antigens. This process results in a PLG particle with gliadin proteins entrapped within (TIMP-GLIA). The solubilization of crude gliadin requires the addition of 10% v/v of trifluoroacetic acid (TFA) in dimethylsulfoxide (DMSO) to facilitate its complete dissolution. When single emulsion is used to formulate TIMP-GLIA particles, PLGA is dissolved in dichloromethane and crude gliadin is solubilized in about 9:1 ratio mixture of DMSO/TFA. (Nature Protocols 4, 1440-1453 (2009)).

While TFA is used to facilitate solvation of crude gliadin, other proteins present in the crude gliadin such as glutenins also become soluble at low pH decreasing the proportion of therapeutic gliadin proteins in the particle formulation. TFA is a strong acid (approximately 34,000 times stronger than acetic acid) that requires special handling and controls to ensure residuals are adequately removed from the TIMP-GLIA particles. TIMP-GLIA particles formed by single emulsion process typically have a particle size of about 1 μm to 4 μm and PDI of about 0.65 to about 1.0 (e.g., 0.8). Due to the presence of higher molecular weight components in TFA solution (e.g., glutenins), potential agglomeration of particles can occur leading to large particle size and high PDI.

Certain embodiments of the present disclosure relate to an alternative method for manufacture TIMP-GLIA to improve gliadin encapsulation and eliminate the use of TFA during formulation. Such process relates to a double-emulsion process (see, e.g., FIG. 2). Double emulsion solvent evaporation methods disclosed herein provide TIMP-GLIA particles without TFA. In some embodiments, PLGA is dissolved in dichloromethane and crude gliadin is extracted by ethanol (e.g. 70%) or acetic acid. Gliadin extract is used as the aqueous phase in the emulsion procedure. While single emulsion may provide a matrix of polymer with antigen dispersed throughout, the disclosed double emulsion process provides a polymer-encapsulated antigen. In a double-emulsion particle, there is less surface-exposed antigen compared to a single-emulsion particle.

In some embodiments, the present disclosure relates to identification and further characterization of crude gliadin extracts for use in TIMP-GLIA production.

It has been found that extraction of crude gliadin preparations with 70% ethanol fortifies the gliadin proteins fraction, due to the differential solubility of gluten proteins (gliadin and glutenin) in this solvent. Using this method, relatively pure gliadin protein preparations can be obtained for further processing in the TIMP-GLIA production process.

In some embodiments, the present disclosure relates to the use of about 50 to about 80% ethanol for extraction of crude gliadin preparations. In certain embodiments, about 50% ethanol is used. In some embodiments, about 60% ethanol is used for extraction. Some embodiments relate to the use of about 65% ethanol. In other embodiments, the extraction is performed with about 70% ethanol. In further embodiments, about 75% ethanol is used. Some other embodiments relate to the use of about 80% ethanol for extraction of gliadin from crude gliadin preparations from wheat.

In some embodiments, the crude extract of gliadin and ethanol are stirred for about 1 to about 3 hours at about 20° C. to about 30° C. (e.g., room temperature) and then centrifuged for about 10 to about 20 min to remove insoluble fractions. The supernatant is filtered and further analyzed.

The protein quantification assay and characterization are done by RP-HPLC and SDS-PAGE. Measured gliadin concentration in about 50% to about 80% ethanol following extraction is at least about 25 mg/mL. SDS-PAGE gel can be used to confirm the presence of gliadins in extract.

Some embodiments of the present disclosure relate to the use of relatively pure gliadin protein preparations in the TIMP-GLIA production process. According to certain embodiments, gliadin extracts in about 50% to about 80% of ethanol provide fortified gliadin proteins fraction, due to the differential solubility of gluten proteins (gliadin and glutenin) in this solvent.

Polymer-encapsulated or conjugated drugs can be more effective than their freely delivered counterparts, since polymer-associated drug is protected from degradation. This protection translates to a longer biological half-life and potentially improved efficacy with reduced systemic side effects.

Biodegradable polymers may be used to make all or some of the polymers and/or particles and/or layers. Biodegradable polymers may undergo degradation, for example, by a result of functional groups reacting with the water in the solution. Composition of the particles has been found to affect the length of time the particles persist in the body and tolerance requires rapid particle uptake and clearance/degradation.

The term "degradation" as used herein refers to becoming soluble, either by reduction of molecular weight or by conversion of hydrophobic groups to hydrophilic groups. Polymers with ester groups are generally subject to spontaneous hydrolysis, e.g., polylactides and polyglycolides.

In certain embodiments, the polymer is biodegradable or biocompatible. In certain embodiments, the polymer is poly (lactide-co-glycolide).

In certain embodiments, the carrier particle is a biodegradble polymer. In other embodiments the particle is poly (lactide-co-glycolide) (PLG) particle. In other embodiments, the carrier particle is a PLURIONICS® stabilized polypropylene sulfide particle.

In some embodiments, the present disclosure provides a process for making compositions (e.g., for induction of antigen-specific tolerance) comprising a carrier particle (e.g., poly(lactide-co-glycolide) (PLG) particle) attached to an antigenic peptide.

Poly(lactic-co-glycolic acid) (PLGA) exhibits many of the ideal properties of a nanoscale delivery system, providing long term release of the encapsulated agent and degrading into the biocompatible products of lactic and glycolic acid. Small molecules, proteins, and nucleic acids that are encapsulated in PLGA have demonstrated enhanced activity in a variety of disease applications (Danhier, F. et al. PLGA-based nanoparticles: An overview of biomedical applications. J. Control. Rel. 161, 505-522 (2012)). Importantly, the material platform facilitates easy customization of features such as size, charge, and surface display of ligands for targeting particles to specific tissues or for imaging purposes.

Oil-water (single) or water-oil-water (double) emulsion is one method by which PLGA can be used to encapsulate hydrophobic and hydrophilic drugs in micro- or nanoscale form. In summary, PLGA is dissolved into an organic phase (oil) that is emulsified with a surfactant or stabilizer (water). Hydrophobic drugs are added directly to the oil phase, whereas hydrophilic drugs (water) may be first emulsified with the polymer solution prior to formation of particles. High intensity homogenization (e.g., sonication bursts) facilitate the formation of small polymer droplets. The resulting emulsion is added to a larger aqueous phase and stirred for several hours, which allows the solvent to evaporate. Hardened nanoparticles are collected and washed by centrifugation. In certain embodiments, hardened emulsion particles can be obtained through evaporation of the oil phase.

Depending on the ratio of lactide to glycolide used for the polymerization, different forms of PLGA can be obtained. These are usually identified in regard to the molar ratio of the monomers used (e.g. PLGA 75:25 identifies a copolymer whose composition is 75% lactic acid and 25% glycolic acid). The ratio of lactide:glycolide monomers in PLGA-can influence degradation rate and drug release. Various ratios can be utilized depending on the implementation and/or application. The particles of the disclosure have a lactide: glycolide ratio of about 50:50. In one embodiment the particles of the disclosure have about a 50:50 D,L-lactide: glycolide ratio.

In one of the embodiments of the present disclosure, as aqueous solution of emulsifier can be added to a single (primary) emulsion formed from of biodegradable polymer (e.g., PLGA) dissolved in organic solvent (oil phase) and the drug or antigen dissolved in aqueous solution (aqueous phase) to provide a double (secondary) emulsion. Addition of an emulsifier provides a stable and homogeneous emulsion.

The high density of carboxylate groups can be achieved by the use of poly(ethylene-alt-maleic anhydride) (PEMA), a polymer with carboxylate groups incorporated into its backbone, as the surfactant for the emulsification process.

In particular embodiments, surface-functionalized biodegradable poly(lactide-co-glycolide) particles with a high density of surface carboxylate groups, synthesized using the surfactant poly(ethylene-alt-maleic anhydride) provide a carrier that offers numerous advantages over other carrier particles and/or surfaces.

Preparation of PLGA particles is generally described in International Publication WO 2014/160465, hereby incorporated in its entirety for all purposes.

Manipulation of the manufacturing process for PLGA particles can control particle properties (e.g. size, size distribution, zeta potential, morphology, hydrophobicity/hydrophilicity, polypeptide entrapment, etc.). The size of the particle is influenced by a number of factors including, but not limited to, the concentration of PLGA, the solvent used in the manufacture of the particle, the nature of the organic phase, the surfactants used in manufacturing, the viscosity of the continuous and discontinuous phase, the nature of the solvent used, the temperature of the water used, sonication, evaporation rate, additives, shear stress, sterilization, and the nature of any encapsulated antigen or polypeptide.

The nature of the polypeptide encapsulated in the particle can affect particle size. In general, encapsulation of hydrophobic polypeptides leads to the formation of smaller particles compared with the encapsulation of more hydrophilic polypeptides. In the double emulsion process, the entrapment of more hydrophilic polypeptides is improved by using high molecular mass PLGA and a high molecular mass of the first surfactant which causes a higher inner phase viscosity. The interaction between the solvent, polymer, and polypeptide affects the efficiency of incorporating the polypeptide into the particle.

The PLGA molecular mass impacts the final mean particle size. In general, the higher the molecular mass, the higher the mean particle size. For example, as the composition and molecular mass of PLGA varies (e.g. 12 to 48 kDa for 50:50 PLGA; 12 to 98 kDa for 75:25 PLGA) the mean particle size varies (about 102 nm-154 nm; about 132 nm to 152 nm respectively). Even when particles are the same molecular mass, their composition can affect average particle size; for example, particles with a 50:50 ratio generally form particles smaller than those with a 75:25 ratio. The end groups on the polymer also affect particle size. For example, particles prepared with ester end-groups form particles with an average size of 740 nm (PI=0.394) compared with the mean size for the acid PLGA end-group is 240 nm (PI=0.225).

Particle size is affected by the polymer concentration; higher particles are formed from higher polymer concentrations. For example, an increase in PLGA concentration from 1% to 4% (w/v) can increase mean particle size from about 205 nm to about 290 nm when the solvent propylene carbonate is used. Alternatively, in ethyl acetate and 5% Pluronic F-127, an increase in PLGA concentration from 1% to 5% (w/v) increases the mean particle size from 120 nm to 230 nm.

The viscosity of the continuous and discontinuous phase is also an important parameter that affects the diffusion process, a key step in forming smaller particles. The size of the particles increases with an increase in viscosity of the dispersed phase, whereas the size of the particles decreases with a more viscous continuous phase. In general, the lower the phase ratio of organic to aqueous solvent, the smaller the particle size.

Homogenizer speed and agitation also affect particle size; in general, higher speeds and agitation cause a decrease in particle size, although there is a point where further increases in speed and agitation no longer decrease particle size. There is a favorable impact in the size reduction when the emulsion is homogenized with a high pressure homogenizer compared with just high stirring. For example, at a phase ration of 20% in 5% PVA, the mean particle size with stirring is 288 nm and the mean particle size with homogenization (high pressure of 300 bars) is 231 nm.

An important size reduction of the particles can be achieved by varying the temperature of the water added to improve the diffusion of the solvent. The mean particle size decreases with an increase in water temperature.

The solvent used can also affect particle size; solvents that reduce the surface tension of the solution also reduce particle size. The organic solvent is removed by evaporation m a vacuum to avoid polymer and polypeptide damage and to promote final particle size reduction. Evaporation of the organic solvent under vacuum is more efficient in forming smaller particles. For example, evaporation in vacuum produces a mean particle size around 30% smaller than the mean particle size produced under a normal rate of evaporation.

The amplitude of the sonication wavelength also affects the particle characteristics. The amplitude of the wavelength should be over 20% with 600 to 800 seconds of sonication to form stable miniemulsions with no more droplet size changes. However, the main draw-back of sonication is the lack of monodispersity of the emulsion formed.

Organic phases that may be used in the production of the particles of the disclosure include, but are not limited to, ethyl acetate, methyl ethyl ketone, propylene carbonate, and benzyl alcohol. The continuous phases that may be used include but are not limited to the surfactant poloxamer 188.

A variety of surfactants can be used in the manufacturing of the particles of the disclosure. The surfactant can be anionic, cationic, or nonionic. Surfactants in the poloxamer and poloaxamines family are commonly used in particle synthesis. Surfactants that may be used, include, but are not limited to PEG (polyethylene glycol), Tween-80, gelatin, dextran, pluronic L-63, PVA (poly(vinyl alcohol)), poly (ethylene-alt-maleic anhydride), methylcellulose, lecithin and DMAB (didodecyldimethylammonium bromide). Additionally, biodegradable and biocompatible surfactants including, but not limited to, vitamin E TPGS (D-a-tocopheryl polyethylene glycol 1000 succinate).

In some implementations, the emulsifier can influence the particle size, and can be selected accordingly.

In certain embodiments, two or more surfactants can be utilized (e.g. in the double emulsion evaporation method). These two surfactants can include a hydrophobic surfactant for the first emulsion, and a hydrophobic surfactant for the second emulsion.

The amount of antigen can also influence the particle size and PDI.

Solvents that may be used in the production of the particles of the disclosure include, but are not limited to, acetone, tetrahydrofuran (THF), chloroform, dichloromethane, methyl chloride, and members of the chlorinate family. In some embodiments, the choice of organic solvents can be based on selection criteria, including: the polymer being soluble in this solvent, and the solvent being completely immiscible with the aqueous phase.

Salts that may be used in the production of the particles of the disclosure include, but are not limited to magnesium chloride hexahydrate, magnesium acetate tetrahydrate.

Salting-out agents may include, but are not limited to, electrolytes (e.g. sodium chloride, magnesium acetate, magnesium chloride), or non-electrolytes (e.g. sucrose).

The stability and size of the particles of the disclosure may be improved by the addition of compounds including, but not limited to, fatty acids or short chains of carbons. The addition of the longer carbon chain of lauric acid is associated with the improvement of particle characteristics. Furthermore, the addition of hydrophobic additives can improve the particle size, incorporation of the polypeptide into the particle, and release profile.

Preparations of particles can be stabilized by lyophilization. The addition of a cryoprotectant such as trehalose can decrease aggregation of the particles upon lyophilization.

Physical properties are also related to a nanoparticle's usefulness after uptake and retention in areas having immature lymphocytes. These include mechanical properties such as rigidity or rubberiness. Some embodiments are based on a rubbery core, e.g., a poly(propylenesulfide) (PPS) core with an overlayer, e.g., a hydrophilic overlayer, as in PEG, as in the PPSPEG system recently developed and characterized for systemic (but not targeted or immune) delivery. The rubbery core is in contrast to a substantially rigid core as in a polystyrene or metal nanoparticle system. The term rubbery refers to certain resilient materials besides natural or synthetic rubbers, with rubbery being a term familiar to those in the polymer arts. For example, cross-linked PPS can be used to form a hydrophobic rubbery core. PPS is a polymer that degrades under oxidative conditions to polysulphoxide and finally polysulphone, transitioning from a hydrophobic rubber to a hydrophilic, water-soluble polymer. Other sulphide polymers may be adapted for use, with the term sulphide polymer referring to a polymer with a sulphur in the backbone of the polymer. Other rubbery polymers that may be used are polyesters with glass transition temperature under hydrated conditions that is less than about 37° C.

A hydrophobic core can be advantageously used with a hydrophilic overlayer since the core and overlayer will tend not to mingle, so that the overlayer tends to sterically expand away from the core. A core refers to a particle that has a layer on it. A layer refers to a material covering at least a portion of the core. A layer may be adsorbed or covalently bound. A particle or core may be solid or hollow. Rubbery hydrophobic cores are advantageous over rigid hydrophobic cores, such as crystalline or glassy (as in the case of polystyrene) cores, in that higher loadings of hydrophobic drugs can be carried by the particles with the rubbery hydrophobic cores.

The particles may incorporate functional groups for further reaction. Functional groups for further reaction include electrophiles or nucleophiles; these are convenient for reacting with other molecules. Examples of nucleophiles are primary amines, thiols, and hydroxyls. Examples of electrophiles are succinimidyl esters, aldehydes, isocyanates, and maleimides.

In some embodiments, the present disclosure provides methods for characterization of TIMP-GLIA particles including such parameters as zeta potential, particle size, dispersity, and antigen loading and/or concentration.

Zeta potential is an important parameter that is related to nanoparticle stability or aggregation in dispersion, and can have significant implications on product performance. The efficacy of colloidal therapeutics, such as the negatively charged particles disclosed herein, is closely related to the particles' in vivo distribution. The distribution of a colloidal system can be predicted by determining the zeta potential. The zeta potential is measure of the potential difference between the dispersion medium and the stationary layer of fluid attached to the dispersed particle, and indicates the degree of repulsion between adjacent, similarly charged particles in a dispersion. A high zeta potential predicts stability and good dispersion of the colloidal formulation. In certain embodiments, the zeta potential of the present pharmaceutical formulations predicts good dispersion of the formulation in vivo.

Laser Doppler Micro-electrophoresis is used to measure zeta potential. An electric field is applied to a solution of molecules or a dispersion of particles, which then move with a velocity related to their zeta potential. This velocity is measured using a patented laser interferometric technique called M3-PALS (Phase analysis Light Scattering). This enables the calculation of electrophoretic mobility and from this the zeta potential and zeta potential distribution.

In some embodiments, the present disclosure provides a process for the preparation an immune modified particle with a negative zeta potential said process comprising: contacting an immune modified particle precursor with a buffer solution under conditions effective to form the immune modified particle with a negative zeta potential. In some embodiments, the immune modified particle precursor is formed by co-polymerization. In some embodiments, the buffer solution has a basic pH.

In some embodiments, buffer solution is sodium bicarbonate, potassium bicarbonate, lithium bicarbonate, potassium dihydrogen phosphate, sodium dihydrogen phosphate, or lithium dihydrogen phosphate.

The particles of the present disclosure can possess a particular zeta potential. In certain embodiments, the zeta potential is negative. In some embodiments, the zeta potential of the particle is from about −100 mV to about 0 mV. In some embodiments, the zeta potential of the particle is from about −50 mV to about −100 mV, inclusive of all ranges and subranges therebetween. In some embodiments, the zeta potential is from about −40 to −80 mV, inclusive of all ranges and subranges therebetween.

In certain embodiments, the particles have a zeta potential of about −80 mV to about +/−0 mV. In certain embodiments, the particles have a zeta potential of about −80 mV to about −40 mV.

The particle may have any particle shape or conformation. However, in some embodiments it is preferred to use particles that are less likely to clump in vivo. Examples of particles within these embodiments are those that have a spherical shape.

In one of the embodiments of the present disclosure, the Dynamic Light Scattering (DLS) is used to measure particle and molecule size. DLS measures the diffusion of particles moving under Brownian motion, and converts this to size and a size distribution using the Stokes-Einstein relationship. Non-Invasive Back Scatter technology (NIBS) is incorporated to give the highest sensitivity simultaneously with the highest size and concentration range. Particle size can be a factor for uptake from the interstitial space into areas of lymphocyte maturation.

The polydispersity index (PDI) or heterogeneity index, or simply dispersity (Đ), is a measure of the distribution of molecular mass in a given polymer sample. Đ calculated is the weight average molecular weight ($M_w$) divided by the number average molecular weight ($M_n$). It indicates the distribution of individual molecular masses in a batch of polymers. Đ has a value equal to or greater than 1, but as the polymer chains approach uniform chain length, Đ approaches unity (1). For some natural polymers Đ is almost taken as unity. Đ (PDI) from polymerization is often denoted as: PDI=$M_w$/$M_n$, where $M_w$ is the weight average molecular weight and $M_n$ is the number average molecular weight. $M_n$ is more sensitive to molecules of low molecular mass, while $M_w$ is more sensitive to molecules of high molecular mass.

In some embodiments of the present disclosure, the polydispersity index (PDI) is less than about 0.3. In some embodiments, the PDI is from about 0.1 to about 0.3.

In certain embodiments of the present disclosure, TIMP-GLIA particles have an average diameter of from about 0.1 μm to about 5 μm. Thus in one embodiment, the particle has a diameter within these limits. In another embodiment, the particle has an average diameter of about 0.2 μm to about 2 μm, and all ranges therebetween. In another embodiment, the particle has an average diameter of about 0.3 m to about 5 μm. In still another embodiment, the particle has an average diameter of about 0.5 μm to about 3 μm. In further embodiments, the particle has an average size of about 0.1 μm, or about 0.2 μm, or about 0.3 μm or about 0.4 μm, or about 0.5 μm, or about 0.6 μm, or about 0.7 μm, or about 0.8 μm, or about 0.9 μm, or about 1.0 μm, or about 1.5 μm or about 2.0 μm or about 2.5 m or about 3.0 m or about 3.5 μm or about 4.0 μm or about 4.5 μm or about 5.0 μm. In a particular embodiment the particle has a size of about 0.4 μm to about 0.8 μm and all ranges therebetween.

In certain embodiments of the present disclosure, gliadin-associated particles have an average diameter of from about 0.1 μm to about 5 μm. Thus in one embodiment, the particle has a diameter within these limits. In another embodiment, the particle has an average diameter of about 0.2 μm to about 2 μm, and all ranges therebetween. In another embodiment, the particle has an average diameter of about 0.3 μm to about 5 μm. In still another embodiment, the particle has an average diameter of about 0.5 μm to about 3 μm. In further embodiments, the particle has an average size of about 0.1 μm, or about 0.2 μm, or about 0.3 μm or about 0.4 μm, or about 0.5 μm, or about 0.6 μm, or about 0.7 μm, or about 0.8 μm, or about 0.9 μm, or about 1.0 μm, or about 1.5 μm or about 2.0 μm or about 2.5 μm or about 3.0 μm or about 3.5 μm or about 4.0 μm or about 4.5 μm or about 5.0 μm. In a particular embodiment the particle has a size of about 0.4 μm to about 0.8 μm and all ranges therebetween.

The particles in a composition need not be of uniform diameter. By way of example, a pharmaceutical formulation may contain a plurality of particles, some of which are about 0.4 μm, while others are about 0.8 μm. Any mixture of particle sizes within these given ranges can be utilized, depending on the implementation and/or application.

Examples of suitable particles include biodegradable polymer particles, polystyrene particles, PLGA particles, PLURIONICS, stabilized polypropylene sulfide particles, and diamond particles.

In one of the embodiments, the particle surface is composed of a material that minimizes non-specific or unwanted biological interactions. Interactions between the particle surface and the interstitium may be a factor that plays a role in lymphatic uptake. The particle surface may be coated with a material to prevent or decrease non-specific interactions. Steric stabilization by coating particles with hydrophilic layers such as poly(ethylene glycol) (PEG) and its copolymers such as PLURONICS® (including copolymers of poly(ethylene glycol)-bl-poly(propylene glycol)-bl-poly (ethylene glycol)) may reduce the non-specific interactions with proteins of the interstitium as demonstrated by improved lymphatic uptake following subcutaneous injections. All of these facts point to the significance of the physical properties of the particles in terms of lymphatic uptake.

Particles of the present disclosure may also contain additional components. For example, carriers may have imaging agents incorporated or conjugated to the carrier. An example of a carrier nanosphere having an imaging agent that is currently commercially available is the Kodak X-sight nanospheres. Inorganic quantum-confined luminescent nanocrystals, known as quantum dots (QDs), have emerged as ideal donors in FRET applications: their high quantum yield and tunable size-dependent Stokes Shifts permit different sizes to emit from blue to infrared when excited at a single ultraviolet wavelength. (Bruchez, et al., Science, 1998, 281, 2013; Niemeyer, C. M. Angew. Chem. Int. Ed. 2003, 42, 5796; Waggoner, A. Methods Enzymol. 1995, 246, 362; Brus, L. E. J. Chem. Phys. 1993, 79, 5566). Quantum dots, such as hybrid organic/inorganic quantum dots based on a class of polymers known as dendrimers, may be used in biological labeling, imaging, and optical biosensing systems. (Lemon, et al., J. Am. Chem. Soc. 2000, 122, 12886). Unlike the traditional synthesis of inorganic quantum dots, the synthesis of these hybrid quantum dot nanoparticles does not require high temperatures or highly toxic, unstable reagents. (Etienne, et. al., Appl. Phys. Lett. 87, 181913, 2005).

The viscosity of the continuous and discontinuous phase is also an important parameter that affects the diffusion process, a key step in forming smaller particles. The size of the particles increases with an increase in viscosity of the dispersed phase, whereas the size of the particles decreases with a more viscous continuous phase. In general, the lower the phase ratio of organic to aqueous solvent, the smaller the particle size.

Molecular Probes CBQCA Protein Quantitation Kit provides a rapid and highly sensitive method for the quantitation of proteins in solution. The kit utilizes the ATTO-TAG CBQCA reagent (3-(4-carboxybenzoyl)quinoline-2-carboxaldehyde) originally developed as a chromatographic derivatization reagent for amines. This reagent has also proven extremely useful for quantitating amines in solution, including the accessible amines in proteins. The ATTO-TAG CBQCA reagent is virtually non-fluorescent in aqueous solution; however, in the presence of cyanide, it reacts with primary amines such as those found in proteins to form highly fluorescent derivatives.

Some embodiments of the present disclosure relate to the particles having an antigen load of about 1 μg/mg-100 μg/mg of PLGA inclusive of all ranges therebetween. In some embodiments, the controllable loading is about 90 μg/mg of PLGA, or about 80 μg/mg of PLGA, or about 70 μg/mg of PLGA, or about 60 μg/mg of PLGA, or about 50 μg/mg of PLGA, or about 40 μg/mg of PLGA, or about 30 μg/mg of PLGA, or about 20 μg/mg of PLGA, or about 10 μg/mg of PLGA. In certain embodiments, the controllable loading is about 1 μg/mg, or about 2 μg/mg, or about 3 μg/mg, or about 4 μg/mg, or about 5 μg/mg, or about 10 μg/mg, or about 15 μg/mg, or about 20 μg/mg of PLGA.

The absolute amount given to each patient depends on pharmacological properties such as bioavailability, clearance rate and route of administration.

Routes of administration include but are not limited to topical, dermal, transdermal, transmucosal, epidermal, parenteral, gastrointestinal, and naso-pharyngeal and pulmonary, including transbronchial and transalveolar.

The present disclosure provides carrier formulations suitable for topical application including, but not limited to, physiologically acceptable implants, ointments, creams, rinses and gels. Exemplary routes of dermal administration are those which are least invasive such as transdermal transmission, epidermal administration and subcutaneous injection.

The term "pharmaceutically acceptable topical formulation", as used herein, means any formulation which is pharmaceutically acceptable for intradermal administration of modified microparticles of the disclosure by application of the formulation to the epidermis. In certain embodiments of the disclosure, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, Remington's Pharmaceutical Sciences, 16th Edition, 1980 and 17th Edition, 1985, both published by Mack Publishing Company, Easton, Pa., the disclosures of which are incorporated herein by reference in their entireties.

In certain other embodiments, the topical formulations of the disclosure may comprise excipients. Non-limiting examples of excipients that can be included in the topical formulations of the disclosure include preservatives, antioxidants, moisturizers, emollients, buffering agents, solubilizing agents, other penetration agents, skin protectants, surfactants, and propellants, and/or additional therapeutic agents used in combination to the modified particles.

Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid.

Suitable moisturizers include, but are not limited to, glycerine, sorbitol, polyethylene glycols, urea, and propylene glycol. Suitable buffering agents for use with the disclosure include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates.

Suitable skin protectants that can be used in the topical formulations of the disclosure include, but are not limited to, vitamin E oil, allatoin, dimethicone, glycerin, petrolatum, and zinc oxide.

In certain embodiments, the pharmaceutically acceptable topical formulations of the disclosure comprise at least the modified particles of the disclosure and a penetration enhancing agent. The choice of topical formulation can depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and Buyuktimkin et al., Chemical-Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, 111. (1997).

In certain exemplary embodiments, penetration agents for use within the scope of the disclosure include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, Ndecylmethylsulfoxide, fatty acid esters (e.g., isopropyl myristate, methyl laurate, glycerol monooleate, and propylene glycol monooleate) and N-methylpyrrolidone.

In certain embodiments, the compositions may be in the form of ointments, pastes, creams, lotions, gels, powders, solutions, sprays, inhalants or patches. In certain exemplary embodiments, formulations of the compositions according to the disclosure are creams, which may further contain saturated or unsaturated fatty acids such as stearic acid, palmitic acid, oleic acid, palmito-oleic acid, cetyl or oleyl alcohols, stearic acid being particularly preferred.

Creams of the disclosure may also contain a non-ionic surfactant, for example, polyoxy-40-stearate. In certain embodiments, the active component is admixed under sterile conditions with a pharmaceutically acceptable carrier and any needed preservatives or buffers as may be required.

Ophthalmic formulation, eardrops, and eye drops are also contemplated as being within the scope of this disclosure. Additionally, the present disclosure contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

Transdermal administration is accomplished by application of a cream, rinse, gel, etc. capable of allowing the carrier to penetrate the skin and enter the blood stream. Compositions suitable for transdermal administration include, but are not limited to, pharmaceutically acceptable suspensions, oils, creams and ointments applied directly to the skin or incorporated into a protective carrier such as a transdermal device (so-called "patch"). Examples of suitable creams, ointments etc. can be found, for instance, in the Physician's Desk Reference. Transdermal transmission may also be accomplished by iontophoresis, for example using commercially available patches which deliver their product continuously through unbroken skin for periods of several days or more. Use of this method allows for controlled transmission of pharmaceutical compositions in relatively great concentrations, permits infusion of combination drugs and allows for contemporaneous use of an absorption promoter.

Parenteral routes of administration include but are not limited to electrical (iontophoresis) or direct injection such as direct injection into a central venous line, intravenous, intramuscular, intraperitoneal, intradermal, or subcutaneous injection. Formulations of carrier suitable for parenteral administration are generally formulated in USP water or water for injection and may further comprise pH buffers, salts bulking agents, preservatives, and other pharmaceutically acceptable excipients. Immunoregulatory polynucleotide for parenteral injection may be formulated in pharmaceutically acceptable sterile isotonic solutions such as saline and phosphate buffered saline for injection.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Gastrointestinal routes of administration include, but are not limited to, ingestion and rectal routes and can include the use of, for example, pharmaceutically acceptable powders, pills or liquids for ingestion and suppositories for rectal administration.

Solid dosage forms for oral administration include capsules, tablets, pills, powders, and granules. In such solid dosage forms, the modified particles are mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (c) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof.

In the case of capsules, tablets and pills, the dosage form may also comprise buffering agents.

Solid compositions of a similar type may also be employed as fillers in soft and hardfilled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The modified particles can also be in micro-encapsulated form with one or more excipients as noted above. The solid dosage forms of tablets, dragees, capsules, pills, and granules can be prepared with coatings and shells such as controlled release and/or other modified-release coatings (e.g., sustained release coatings, enteric coatings, and lag-time coatings, and various combinations thereof).

In such solid dosage forms the active compound may be admixed with at least one inert diluent such as sucrose, lactose and starch. Such dosage forms may also comprise additional substances other than inert diluents, e.g., tableting lubricants and other tableting aids such as magnesium stearate and microcrystalline cellulose.

In the case of capsules, tablets and pills, the dosage forms may also comprise buffering agents. They may optionally contain opacifying agents and can also be of a composition that they release the modified particles only, or preferentially, in a certain part of the intestinal tract, optionally, in a delayed manner. Examples of embedding compositions which can be used include polymeric substances and waxes.

Naso-pharyngeal and pulmonary administration include are accomplished by inhalation, and include delivery routes such as intranasal, transbronchial and transalvcolar routes. The disclosure includes formulations of carrier suitable for administration by inhalation including, but not limited to, liquid suspensions for forming aerosols as well as powder forms for dry powder inhalation delivery systems.

Devices suitable for administration by inhalation of carrier formulations include, but are not limited to, atomizers, vaporizers, nebulizers, and dry powder inhalation delivery devices.

The modified particles can be administered by aerosol. This is accomplished by preparing an aqueous aerosol, liposomal preparation or solid particles containing the modified particles. A nonaqueous (e.g., fluorocarbon propellant) suspension could be used.

Ordin

TABLE 1-continued

Solubility testing of crude gliadin obtained from Sigma-Aldrich in a variety of solvents.

| Conditions | Concentration of crude gliadin | Solubility | Analysis concentration* | Solubility after dilution in Solvent A |
|---|---|---|---|---|
| 70% ethanol | 10 mg/mL | SS | 1 mg/mL | S |
| Acetic acid | 10 mg/mL | SS | 1 mg/mL | S |
| TFA | 10 mg/mL | S | 1 mg/mL | PS |
| DMSO/TFA (9:1) | 40 mg/mL | S | 1 mg/mL | SS |

S. Soluble; SS: Sightly soluble; PS: poorly soluble.
*samples diluted with solvent A(15% acetonitrile + 0.1% TFA).

Solubility of gliadin extracts was also evaluated following dilution in HPLC solvent A (15% acetonitrile+0.1% TFA). All ethanol samples following dilution in solvent A remained soluble, whereas solubilized TFA and DMSO/TFA mixtures precipitated out of solution following addition of solvent A.

Figure 5B:
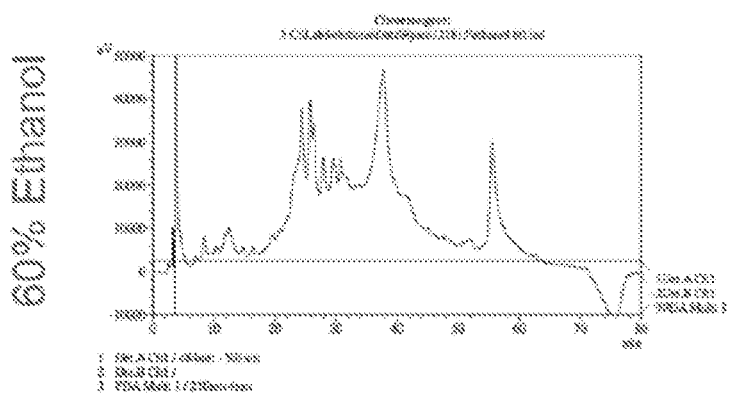
Figure 5C:
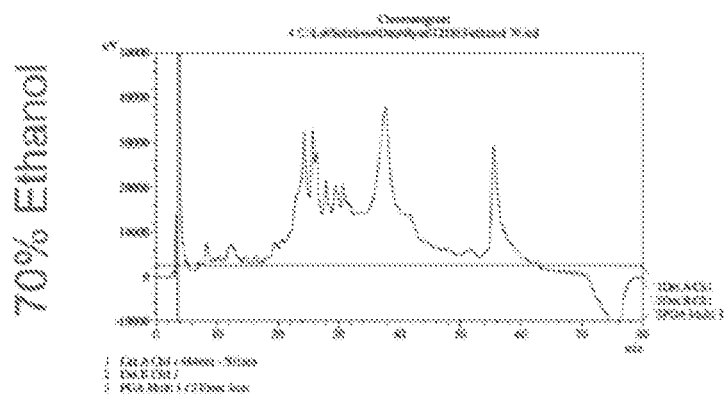
Figure 5D:
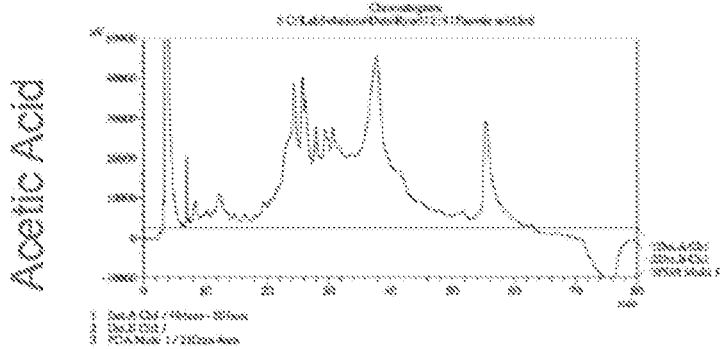
Figure 5E:
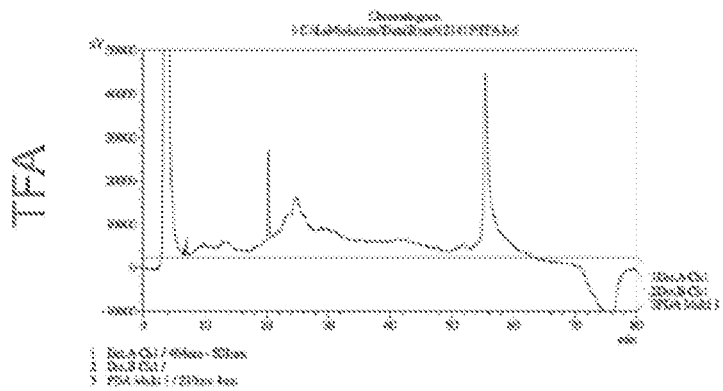
Figure 5F:
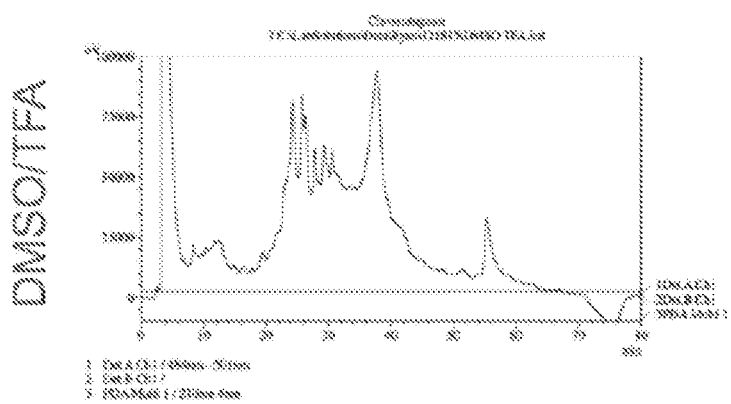

Crude gliadin extract was slightly soluble in increasing concentrations ethanol (50-70%) and acetic acid, whereas the use of TFA or a mixture of DMSO/TFA led to complete solubilization. For analysis of the solubilized fractions of gliadin in the various solvents by RP-HPLC, each sample was centrifuged, and the solute was diluted 10-fold in RP-HPLC mobile phase (solvent A) and observed for maintenance of solubility. All gliadin extracts remained soluble following dilution except TFA and DMSO:TFA samples where precipitate was observed. These samples were re-centrifuged and the supernatants were subsequently analyzed. RP-HPLC chromatograms of crude gliadin extracted from the various solvents are shown in FIG. 5. Profiles of gliadin extracts obtained from all ethanol samples were nearly identical, whereas the gliadin samples extracted with acetic acid had a similar profile with additional peaks and a larger area under the curve (AUC), indicating that acetic acid solubilized additional proteins as compared to ethanol. The DMSO:TFA samples, also displayed similar profile with some minor differences, although was not fully compatible with the HPLC solvent system. Given the large amount of precipitate formed following dilution in the RP-HPLC mobile phase for the TFA sample, a weak signal and poor peak resolution was observed.

Identification Of Alternate Sources For Gliadin Extracts: Initial RP-HPLC results indicated similar profiles for solubilized crude gliadin extract in ethanol (50-70%) and acetic acid. The method used for extraction of gliadins from different sources could potentially impact the composition of gliadin proteins within the crude extracts. To address this, crude gliadin extract was obtained from Sigma-Aldrich and MP Biochemical, and compared in both 70% ethanol and acetic acid extraction processes. Comparisons were performed using the CBCQA protein quantitation assay, RP-HPLC, SDS-PAGE, and LC-MS.

Protein samples of crude gliadin extracts from each source were solubilized in 70% ethanol and acetic acid, and their concentrations were determined by the CBQCA protein assay (Table 2). Total protein content in samples extracted using the same solvent was generally consistent. Acidic acid extract samples showed significantly increased protein levels. Similarly, RP-HPLC results showed an increased area under the curve for acetic acid extracts (FIG. 5).

RP-HPLC chromatograms of 50% (FIG. 5A), 60% (FIG. 5B), and 70% (FIG. 5C) ethanol and acetic acid (FIG. 5D) gliadin extracts obtained from Sigma. Each sample was analyzed following 24 hr extraction of crude gliadin extracts at a concentration of 10 mg/mL. Samples were detected at 210 nm. Sigma crude gliadin extracts from 70% ethanol contain similar proportions of gliadins. Acetic acid extraction of crude extracts yields a greater amount of protein as measured by the increased area under the curve for gliadins. The cleaner appearance of the gliadins by HPLC provides evidence that ethanol extraction can be more compatible for particle development then other solvents tested, according to some embodiments.

Preparatory SDS-PAGE and LC-MS results demonstrates the presence of alpha/beta and gamma gliadins in both gliadin extract source samples using either 70% ethanol or acetic acid as the solvent (FIG. 11 and Table 5). Although samples prepared with acetic acid contained the expected gliadin fraction, they also contained HMW glutenin fractions. Taken together, these experiments suggest that 70% ethanol extracts from either Sigma-Aldrich or MP Biomedical contain the required gliadin proteins. Extraction with acetic acid also contained gliadins, however the proportion of glutenins was greatly increased.

TABLE 2

Measured total protein concentration of gliadin extraction from crude Sigma-Aldrich or MP gliadin using CBQCA assay.

| Source | Extraction Method | #1 (mg/mL) | #2 (mg/mL) |
|---|---|---|---|
| Sigma | 70% ethenol | 26.8 | 25.3 |
| Sigma | Acetic Acid | NA | NA |
| MP | 70% ethenol | 43.3 | 27.6 |
| MP | Acetic Acid | 75.2 | 75 |

100 mg/mL of crude gliadin was incubated for 1 hr in the various solvents indicated. Total protein was quantified against a standard curve of lyophilized 70% gliadin extracts from either Sigma-Aldrich or MP. No standard curve from lyophilized material extracted by acetic acid was generated due to the inability to remove the solvent and obtain a powder form. Acetic acid concentration was determined against a standard curve of lyophilized 70% ethanol extract from the appropriate vendor. Sigma-Aldrich gliadin acetic acid extract was not measured.

Each sample was analyzed following 1 hr extraction of crude gliadin extracts at a concentration of 5 mg/mL. Samples were detected at 210 nm. Sigma and MP Biomedical crude gliadin extracts from 70% ethanol contain similar proportions of gliadins. Acetic acid extraction of crude extracts yields a greater amount of protein as measured by the increased area under the curve for gliadins (see, e.g., FIG. 6A-D).

Stress Testing Of Gliadin: The above discussion indicates the suitability of 70% ethanol as an alternative to the use of DMSO/TFA for solubilization of gliadins for use in TIMP-GLIA manufacturing. To further characterize the differences between crude gliadin extracts from Sigma-Aldrich and MIP Biomedical, and to determine the effect of process conditions on these extracts, a series of stress degradation tests were performed. In this section, the effect of sonication time, temperature, lyophilization, and solvent mixtures were evaluated by RP-HPLC.

The RP-HPLC results for 70% ethanol extracted crude gliadins from Sigma-Aldrich and MP Biomedical following sonication for 30 s, 60 s, and 120 s is shown in FIG. 7. Compared to unsonicated controls, sonication did not appear to cause significant degradation up to 60 s. At 120 seconds sonication, peak elution times and profiles remained consistent, but AUC for gliadins was reduced. Samples were detected at 210 nm. Sonication did not appear to alter the elution of analyzed proteins.

The effect of temperature on gliadin samples is shown in FIG. 8. Crude gliadin extracts from Sigma-Aldrich and MP Biomedical were extracted with 70% ethanol and were incubated at ambient, 37° C., and 60° C. overnight. Both 37° C. and 60° C. appeared to have an effect on peak profile and area, with 60° C. being significantly more pronounced. Samples were detected at 210 nm. Increased temperatures affected MP gliadin greater than Sigma gliadin. Heating of gliadin samples to greater than 37° C. for long periods of time is not recommended.

The effect on lyophilization on Sigma-Aldrich and MP Biomedical crude gliadin after further processing with 70% ethanol is shown in FIG. 9. Analysis by RP-HPLC indicated that MP Biomedical gliadin was significantly affected by the current lyophilization process.

MP Biomedical gliadins displayed altered protein elution characteristics compared to non-lyophilized controls, whereas Sigma-Aldrich gliadin did not show any noticeable changes. These results suggested that Sigma-Aldrich gliadin is more stable during the lyophilization process as compared to gliadin from MP Biomedical.

Comparison of the HPLC chromatograms of 70% ethanol extracted gliadin versus 70% ethanol extracted and lyophilized gliadin: lyophilization appeared to significantly affect the gliadin from MP Biomedical. The lyophilized extract was used to generate the standard curves for CBQCA assay to determine TIMP-GLIA loading.

Dimethylsulfoxide (DMSO) is a solvent used for the dissolution of TIMP-GLIA for loading characterization. Therefore, it was necessary to understand its effects on gliadin proteins. 70% Ethanol extracted gliadins (extracted with 70% ethanol) from Sigma-Aldrich and MP Biomedical were diluted in DMSO and analyzed by RP-HPLC analysis (FIG. 10).

HPLC chromatograms of 70% ethanol gliadin extracts obtained from Sigma or MP Biomedical were mixed with DMSO. Samples were detected at 210 nm. Mixing with DMSO did not appear to alter the elution profiles of the proteins in the samples. Mixing of gliadin extracts with DMSO did not significantly alter the protein elution characteristics. It should be noted that DMSO did significantly broaden the injection peak at 2 min. It should be noted that loading of gliadin within TIMP-GLIA is measured by CBQCA protein assay and not by RP-HPLC. These results indicate that DMSO is an acceptable solvent for dissolution of TIMP-GLIA.

Example 1a. Purification of Gliadin Extract from Wheat 1 gram of Gliadin from wheat (e.g., Sigma-Aldrich, Cat No G3375) and 10 mL of 70% ethanol (e.g., Sigma, Cat No. 459844)) were added to a 20 mL vial equipped with a stir bar and vortexed to ensure that the sample is dispersed well. The stirring was continued for 1 hour at room temperature. The sample was transferred to a 50 mL conical tube and centrifuge for 10 min at 7000×g to remove insoluble fractions (e.g., Thermo Scientific Sorvall Legend Centrifuge or equivalent (capable of centrifuging 50 mL conical tubes at 7000×g)). The supernatant was filtered through a 40 m cell strainer into another 50 mL conical tube. The extract sample may be slightly cloudy. Slight warming of the extract to 30° C. for 10 min will improve its clarity and solubility.

The protein quantification assay and characterization were done by RP-HPLC and SDS-PAGE. Measured gliadin concentration in 70% ethanol following extraction was greater than 25 mg/mL. SDS-PAGE gel confirmed the presence of gliadins in extract.

Example 1b. Separation of Gliadin Proteins by RP-HPLC

HPLC analysis was carried out following a method developed by Bietz et al. (Gliadin Analysis by Reversed-Phase High-Performance Chromatography: Optimization of Extraction Conditions. Bietz et al. (1984), Cereal Chem 61).

Gliadin detection conditions: Gliadin extract concentration in 70% ethanol is between about 1 mg/mL and about 5 mg/mL for analysis. PDA about 210 nm; column temperature about 26° C.; Flow rate about 1 mL/min; Injection volume about 50 µL.

A binary linear gradient was setup with Solvent A (15% Acetonitrile+0.1% Trifluoroacetic acid) and Solvent 13 (85% Acetonitrile+0.1% Trifluoroacetic acid) at 1 mL/min. Solvent B was varied from about 20-55% from about 0 to about 55 min and held at about 55% for about 10 additional min (about 65 min total). Solvent B was then ramped down linearly to about 20% over about 5 min (about 70 min total). Solvent B was the held constant at about 20% for about 10 min prior to the next injection for baseline stabilization (about 80 min total).

Acceptance criteria include observation of omega, alpha, beta, and gamma fractions of gliadin in chromatograms (Evaluation and Characterization of Gliadin Nanoparticles and Isolates by Reversed-Phase HPLC. Arangoa et al. (2000), J Cereal Sci 31). Reference Reversed Phase High-Performance Liquid Chromatography (RP-HPLC) using the described method is shown in FIG. 3.

Example 1c. Separation of Gliadin Proteins by SDS-PAGE Analysis

Sodium dodecyl sulfate-polyacrylamide gel electrophoresis (SDS-PAGE) is used to separate and characterize proteins and other macromolecules. SDS-PAGE uses a polyacrylamide gel and SDS to induce protein denaturation. SDS is an anionic surfactant that imparts a negative charge on the proteins in solution that enables them to be separated by an electric field.

The procedure includes the following:

Clamp in gel (e.g., BIO-RAD Mini-PROTEAN TGX Stain-Free Precast Gels (e.g., BIO-RAD, Cat No. 456-8084)) and fill both buffer chambers with gel running buffer (e.g., SDS Running Buffer) according to the manufacturer instructions. Ensure to include a lane with protein molecular mass standards (5 µL of unstained protein standard (e.g., BIO-RAD unstained protein standard (e.g., BIO-RAD, Cat No. 1610363)) into lane 1.

Sample preparation for purified gliadin extract (Cour Pharma): Prepare about 1 µg of purified gliadin extract in about 15 µL 70% ethanol in a 1.5 mL microcentrifuge tube. Add about 15 µL of 2× Laemmli sample buffer (e.g., BIO-RAD 2× Laemmli Sample buffer (e.g., BIO-RAD, Cat No. 161-0737)) to the sample. Add about 1.5 µL of 2-mercaptoethanol (e.g., BIO-RAD 2-Mercaptoethanol (BIO-RAD, Cat No. 161-0710)) to the sample. Heat the sample at about 95° C. for about 5 min. Load the entire sample into the gel.

Sample preparation for TIMP-GLIA: Measure the loading of TIMP-GLIA using the CBQCA (3-(4-carboxybenzoyl)

quinoline-2-carboxaldehyde) assay. Prepare a TIMP-GLIA solution in DMSO such that the concentration of gliadin is about 1 µg gliadin/about L DMSO in a 1.5 mL microcentrifuge tube. Add about 15 µL of 2× Laemmli sample buffer to the sample. Add about 1.5 µL 2-mercaptoethanol to the sample. Heat the sample at about 95° C. for about 5 min. Load the entire sample into the gel. Run the gel for about 60 min at about 110 V and about 3 amps. Remove the gel from the cassette and image using a gel imaging system.

Inclusion of a protein ladder on each gel will enable determination of relative molecular mass of the gliadins. The molecular mass standards should encompass the 250 kD to 15 kD regions on the gel.

Detectable bands of similar molecular mass to gliadins (see reference gel, FIG. 4). FIG. 4 can serve as a reference standard for comparison.

Example 2. Utilization of a Double Emulsion Process in the Production of TIMP-GLIA Particles One method for TIMP-GLIA manufacturing utilizes a single emulsion solvent evaporation technique (FIG. 1). However, this method requires both the gliadin and the polymer used for encapsulation to be soluble in miscible solvents. As poly(lactide-co-glycolide) (PLGA) is solubilized in dichloromethane, the solvation of crude gliadin was performed using a 9:1 ratio of DMSO to TFA. The goal of this investigation was to remove the use of TFA during the manufacturing process of TIMP-GLIA. To remove TFA from the formulation of TIMP-GLIA, the feasibility of using a double emulsion solvent evaporation method (FIG. 2) with gliadin extracts purified using 70% ethanol or acetic acid was evaluated.

Twenty-two formulations were evaluated using various TIMP-GLIA manufacturing conditions as described in Table 3. Conditions evaluated included the formulation of TIMP-GLIA from purified and lyophilized gliadin powder, acetic acid extracted gliadin, and 70% ethanol extracted gliadin. Variables such as gliadin concentration, volume of gliadin, and gliadin source vendor were also evaluated. An emphasis on Sigma-Aldrich gliadin was made due to its performance in the above described studies.

TIMP-GLIA particles were characterized for their size, zeta potential, polydispersity index (PDI), gliadin loading, and encapsulation efficiency (Table 4). Formulation of TIMP-GLIA particles using 70% ethanol extract from Sigma-Aldrich proved to be most effective as demonstrated by sizes between 400-800 nm, zeta potentials less than −40 mV, and PDI less than 0.3. Note: at temperatures less than 25° C. the gliadin extract solubility/clarity decreases. Prior to particle fabrication, the gliadin extract solution was heated slightly (~25-30° C.) for 5-10 min to improve its solubility/clarity. Interestingly, the loading of gliadin within TIMP-GLIA was found to be proportional to the concentration of gliadin in the Sigma-Aldrich gliadin 70% ethanol extract (TIMP-GLIA011 to TIMP-GLIA014). TIMP-GLIA008, TIMPGLIA009, TIMP-GLIA010, and TIMP-GLIA003 were subjected to SDS-PAGE analysis (FIG. 11) and protein characterization by LC-MS (Table 5). SDS-PAGE gel compares MP Biomedical and Sigma crude gliadin extracts from 70% ethanol and acetic acid (AA) and TIMP-GLIA008, TIMP-GLIA009, TIMP-GLIA010, and TIMP-GLIA003.

In the SDS-PAGE gel, the gliadin proteins within the region of 25 to 37 kD were stained weakly (not noticeable for TIMP-GLIA003). LC-MS characterization of the protein contents within that region demonstrated the presence of appropriate gliadin fractions within the TIMP-GLIA formulations except TIMP-GLIA003. To clearly observe gliadin fractions within TIMP-GLIA008, another SDS-PAGE gel was run (FIG. 12). Clear bands in the gel compared to control demonstrated the successful encapsulation of gliadin fractions within TIMP-GLIA008. Based on this data, it was concluded that the most favorable method for TIMP-GLIA manufacturing would be to use 70% ethanol extracted gliadin from Sigma-Aldrich in the TIMP-GLIA formulation using the double emulsion method.

TABLE 3

TIMP-GLIA manufacturing conditions attempted.

| Batch | Lyophilized or extract | Solvent | Concentration of Gliadin | Vendor | Volume of gliadin added |
| --- | --- | --- | --- | --- | --- |
| TIMP-GLIA001 | Lyophilized | 70% ethanol | 100 mg/mL | MP | 150 µL |
| TIMP-GLIA002 | Lyophilized | 70% ethanol | 50 mg/mL | MP | 300 µL |
| TIMP-GLIA003 | Lyophilized | 70% ethanol | 25 mg/mL | MP | 600 µL |
| TIMP-GLIA004 | Lyophilized | DMSO | 25 mg/mL | MP | 400 µL |
| TIMP-GLIA008 | Extract | 70% ethanol | Not measured | Sigma | 600 µL |
| TIMP-GILA009 | Extract | 70% ethanol | Not measured | MP | 600 µL |
| TIMP-GLIA010 | Extract | Acetic acid | Not measured | Sigma | 600 µL |
| TIMP-GLIA011 | Extract | 70% ethanol | 25 mg/mL | Sigma | 600 µL |
| TIMP-GLIA012 | Extract | 70% ethanol | 20 mg/mL | Sigma | 600 µL |
| TIMP-GLIA012.2 | Extract | 70% ethanol | 20 mg/mL | Sigma | 600 µL |
| TIMP-GLIA013 | Extract | 70% ethanol | 15 mg/mL | Sigma | 600 µL |
| TIMP-GLIA014 | Extract | 70% ethanol | 10 mg/mL | Sigma | 600 µL |

TABLE 3-continued

TIMP-GLIA manufacturing conditions attempted.

| Batch | Lyophilized or extract | Solvent | Concentration of Gliadin | Vendor | Volume of gliadin added |
|---|---|---|---|---|---|
| TIMP-GLIA015 | Extract | 70% ethanol | 25 mg/mL | Sigma | 600 μL |
| TIMP-GLIA016 | Extract | 70% ethanol | 25 mg/mL | Sigma | 600 μL |
| TIMP-GLIA017 | Extract | 70% ethanol | 10 mg/mL | Sigma | 600 μL |
| TIMP-GLIA018 | Extract | 70% ethanol | 10 mg/mL | Sigma | 600 μL |
| TIMP-GLIA019 | Extract | 70% ethanol | 25 mg/mL | Sigma | 600 μL |
| TIMP-GLIA020 | Extract | 70% ethanol | 25 mg/mL | Sigma | 600 μL |
| TIMP-GLIA021 | Extract | 70% ethanol | 10 mg/mL | Sigma | 600 μL |
| TIMP-GLIA022 | Extract | 70% ethanol | 10 mg/mL | Sigma | 600 μL |

All TIMP-GLIA were prepared using the double emulsion method as described above. Numbers measured by CBQCA assay using a standard curve of 70% ethanol extracted and lyophilized gliadin from the appropriate vendor. Briefly, 2 mL of 200 mg/mL PLGA in dichloromethane was added to a 20 mL scintillation vial. The indicated volume of gliadin solution was added slowly. The sample was sonicated for 30 s prior to immediately adding 10 mL of 1% poly (ethylene-alt-maleic anhydride) (PEMA) and subsequent sonication. After sonication, the emulsion was immediately poured into 200 mL of a 0.5% PEMA solution. The particles were allowed to stir overnight to harden in 0.5% PEMA before they were recovered the following day.

TABLE 4

Summary of TIMP-GLIA particles fabricated using a double emulsion method using 70% ethanol extracted gliadin from Sigma-Aldrich. Particle loading was measured by the CBQCA assay using a standard curve using 70% ethanol extracted and lyophilized gliadin from the same vendor (MP Biomedical or Sigma-Aldrich). TIMP-GLIA as well as the lyophilized extracts are easily dissolved in 100% DMSO.

| Particle | Size (nm) | Zeta petential (mV) | PDI | Loading (μg/mg)* | Encapsulation efficiency (%) |
|---|---|---|---|---|---|
| TIMP-GLIA001 | 427.4 ± 13.9 | −46.5 ± 1.1 | 0.427 | 0.44 ± 0.14 | 1.2 ± 0.14 |
| TIMP-GLIA002 | 496.6 ± 6.4 | −46.2 ± 0.3 | 0.451 | 1.59 ± 0.36 | 4.2 ± 0.36 |
| TIMP-GLIA003 | 678.3 ± 8.1 | −43.9 ± 1.0 | 0.525 | 3.42 ± 0.30 | 9.1 ± 0.30 |
| TIMP-GLIA004 | 472.7 ± 7.1 | −41.9 ± 0.6 | 0.387 | 1.46 ± 0.31 | 4.0 ± 0.31 |
| TIMP-GLIA008 | 665.2 ± 30 | −51.5 ± 2.5 | 0.294 | 13.7 ± 0.28 | 34.2 ± 0.7 |
| TIMP-GLIA009 | 1568 ± 128 | −45.1 ± 0.6 | 0.854 | 10.8 ± 1.0 | 16.7 ± 1.5 |
| TIMP-GLIA010 | 1154 ± 78 | −47.3 ± 1.0 | 6.733 | 22.8 ± 1.7 | 20.2 ± 1.5 |
| TIMP-GLIA011 | 595.1 ± 9.1 | −43.6 ± 0.5 | 0.215 | 16.2 ± 1.0 | 43.1 ± 2.7 |
| TIMP-GLIA012 | 707.2 ± 15 | −48.4 ± 0.2 | 0.422 | 12.8 ± 0.7 | 42.8 ± 2.2 |
| TIMP-GLIA012.2 | 695.6 ± 23 | −46.9 ± 0.6 | 0.216 | 11.1 ± 0.6 | 36.9 ± 2.0 |
| TIMP-GLIA013 | 958.8 ± 46 | −43.6 ± 0.8 | 0.405 | 8.5 ± 0.5 | 37.9 ± 2.3 |
| TIMP-GLIA014 | 535.9 ± 2.9 | −45.0 ± 0.3 | 0.344 | 4.0 ± 0.1 | 26.8 ± 0.7 |
| TIMP-GLIA015 | 895.7 ± 10 | −44.2 ± 0.2 | 0.121 | 20.3 ± 0.6 | 54.1 ± 1.6 |
| TIMP-GLIA016 | 714.4 ± 5.6 | −40.4 ± 2 | 0.196 | 16.1 ± 2.1 | 42.8 ± 5.5 |
| TIMP-GLIA017 | 599.1 ± 18 | −47.6 ± 0.1 | 0.226 | 5.5 ± 0.6 | 36.5 ± 3.7 |
| TIMP-GLIA018 | 602.2 ± 15 | −45.8 ± 1 | 0.240 | 6.57 ± 1.7 | 43.8 ± 12 |

TABLE 4-continued

Summary of TIMP-GLIA particles fabricated using a double emulsion
method using 70% ethanol extracted gliadin from Sigma-Aldrich. Particle
loading was measured by the CBQCA assay using a standard curve using
70% ethanol extracted and lyophilized gliadin from the same vendor
(MP Biomedical or Sigma-Aldrich). TIMP-GLIA as well as the lyophilized
extracts are easily dissolved in 100% DMSO.

| Particle | Size (nm) | Zeta petential (mV) | PDI | Loading (μg/mg)* | Encapsulation efficiency (%) |
|---|---|---|---|---|---|
| TIMP-GLIA019 | 789.0 ± 13 | −43.7 ± 1 | 0.123 | 16.4 ± 1.1 | 43.7 ± 2.9 |
| TIMP-GLIA020 | 711.8 ± 14 | −41.4 ± 0.6 | 0.280 | 14.3 ± 0.6 | 38.0 ± 1.7 |
| TIMP-GLIA021 | 538.5 ± 12 | −45.6 ± 0.3 | 0.172 | 5.6 ± 1.1 | 37.6 ± 7.4 |
| TIMP-GLIA022 | 596.8 ± 7 | −44.9 ± 0.3 | 0.276 | 4.6 ± 0.2 | 30.5 ± 1.6 |

TABLE 5

Protein identification from an SDS-PAGE gel region between 25-37
kD (FIG. 3.4.3) with in-gel digestion with pepsin/chymotrypsin
and elastase. LC-MS/MS was performed followed by database searches
and reporting of proteins identified by sequence.

| # | Identified Proteins (35) | Accession Number | Molecular Weight | MP 70% ethanol |
|---|---|---|---|---|
| 1 | Alpha-gliadin OS = *Triticum aestivum* GN = Gli-Z1 PE = 2 SV = 3 | tr\|Q1WA39\|Q1WA39_WHE | 35 kDa | 96 |
| 2 | Glutenin, low molecular weight subunit 1D1 OS = *Triticum aestivum* PE | sp\|P10386\|GLTB_WHEAT | 35 kDa | 69 |
| 4 | Gamma-gliadin OS = *Triticum aestivum* PE = 3 SV = 1 | sp\|P08453\|GD82_WHEAT | 37 kDa | 69 |
| 5 | Alpha/beta-gliadin OS = Triticum aestivum PE = 2 SV = 2 | sp\|P02863\|GDA0_WHEAT | 33 kDa | 155 |
| 8 | Alpha/beta-gliadin A-V OS = Triticum aestivum PE = 2 SV = 1 | sp\|P04725\|GDA5_WHEAT | 37 kDa | 126 |
| 9 | Gamma-gliadin OS = *Triticum aestivum* GN = 11908 PE = 2 SV = 1 | tr\|B6UKM9\|B6UKM9_WHE | 33 kDa | 46 |
| 10 | Glutenin, low molecular weight subunit OS = *Triticum aestivum* PE = 3S | sp\|P10385\|GLTA_WHEAT | 41 kDa | 26 |
| 11 | Gamma-gliadin OS = *Triticum aestivum* PE = 3 SV = 1 | sp\|P21292\|GDBX_WHEAT | 34 kDa | 44 |
| 12 | Gamma-gliadin B OS = *Triticum aestivum* PE = 3 SV = 1 | sp\|P06659\|GDBB_WHEAT | 33 kDa | 51 |
| 13 | Alpha/beta-gliadin A-IV OS = Triticum aestivum PE = 2 SV = 1 | sp\|P04724\|GDA4_WHEAT | 34 kDa | 90 |
| 14 | Alpha/beta-gliadin A-II OS = Triticum aestivum PE = 2 SV = 1 | sp\|P04722\|GDA2_WHEAT | 34 kDa | 100 |
| 15 | Gamma-gliadin B-I OS = Triticum aestivum PE = 2 SV = 1 | sp\|P04729\|GDB1_WHEAT | 34 kDa | 26 |

TABLE 5-continued

Protein identification from an SDS-PAGE gel region between 25-37 kD (FIG. 3.4.3) with in-gel digestion with pepsin/chymotrypsin and elastase. LC-MS/MS was performed followed by database searches and reporting of proteins identified by sequence.

| # | Protein | Accession | MW | Score |
|---|---|---|---|---|
| 16 | Alpha/beta-gliadin A-III OS = Triticum aestivum PE = 2 SV = 1 | sp|P04723|GDA3_WHEAT | 32 kDa | 41 |
| 17 | LMW-glutenin P3-6 OS = Triticum aestivum GN = lmw-gs PE = 4 SV = 3 | tr|Q8W3V4|Q8W3V4_WHE | 34 kDa | 0 |
| 18 | Alpha/beta-gliadin clone PW1215 OS = Triticum aestivum PE = 3 SV = 1 | sp|P04726|GDA6_WHEAT | 34 kDa | 76 |
| 19 | Gamma-gliadin (Fragment) OS = Triticum aestivum PE= 2 SV = 1 | sp|P08079|GDB0_WHEAT | 29 kDa | 0 |
| 20 | Alpha/beta-gliadin clone PW8142 OS = Triticum aestivum PE = 3 SV = 1 | Sp|P04727|GDA7_WHEAT | 36 kDa | 74 |
| 21 | Avenin-like b6 OS = Triticum aestivum PE = 3 SV = 1 | sp|A5A4L4|AVLB6_WHEAT | 32 kDa | 0 |
| 22 | Alpha/beta-gliadin A-I OS = Triticum aestivum PE = 2 SV = 1 | sp|P04721|GDA1_WHEAT | 30 kDa | 126 |
| 25 | Gliadin/avenin-like seed protein OS = Triticum aestivum PE = 2 SV = 1 | tr|D2KFG9|D2KFG9_WHEAT | 22 kDa | 0 |
| 26 | Glutenin, high molecular weight subunit DY10 OS = Triticum aestivum | sp|P10387|GLT0_WHEAT | 70 kDa | 0 |
| 29 | Glutenin, high molecular weight subunit DX5 OS = Triticum aestivum | sp|P10388|GLT5_WHEAT | 90 kDa | 0 |
| 30 | Alpha/beta-gliadin clone PTO-A10 (Fragment) OS = Triticum aestivum | sp|P04728|GDA8_WHEAT | 22 kDa | 0 |
| 31 | Non-specific serine/threonine protein kinase OS = Triticum aestivum G | tr|W5H4R1|W5H4R1_WHE | 55 kDa | 0 |
| 32 | Avenin-like a5 OS = Triticum aestivum PE = 3 SV = 1 | sp|P0CZ09|AVLA5_WHEAT | 19 kDa | 0 |
| 33 | Avenin-like b4 OS = Triticum aestivum PE = 3 SV = 1 | sp|A5A4L5|AVLB4_WHEAT | 33 kDa | 0 |
| 34 | Serpin-Z1B OS = Triticum aestivum PE = 1 SV = 1 | sp|P93693|SPZ1B_WHEAT | 43 kDa | 0 |
| 35 | Avenin-like a4 OS = Triticum aestivum PE = 2 SV = 1 | sp|D2KFH1|AVLA4_WHEAT | 19 kDa | 0 |

| # | Sigma 70% ethanol | MP acetic acid | Sigma acetic acid | TIMP-GLIA008 | TIMP-GLIA009 | TIMP-GLIA010 | TIMP-GLIA003 |
|---|---|---|---|---|---|---|---|
| 1 | 57 | 146 | 139 | 17 | 10 | 12 | 0 |
| 2 | 51 | 188 | 148 | 19 | 14 | 8 | 4 |
| 4 | 41 | 93 | 68 | 14 | 17 | 14 | 0 |
| 5 | 87 | 207 | 162 | 12 | 12 | 25 | 0 |
| 8 | 88 | 175 | 148 | 11 | 0 | 26 | 0 |
| 9 | 16 | 84 | 65 | 0 | 0 | 0 | 0 |
| 10 | 13 | 73 | 43 | 0 | 0 | 0 | 0 |
| 11 | 26 | 90 | 60 | 0 | 0 | 0 | 0 |
| 12 | 7 | 98 | 67 | 0 | 0 | 0 | 0 |
| 13 | 57 | 136 | 117 | 0 | 0 | 18 | 0 |

TABLE 5-continued

Protein identification from an SDS-PAGE gel region between 25-37 kD (FIG. 3.4.3) with in-gel digestion with pepsin/chymotrypsin and elastase. LC-MS/MS was performed followed by database searches and reporting of proteins identified by sequence.

| 14 | 61 | 155 | 138 | 11 | 0 | 16 | 0 |
| 15 | 12 | 68 | 37 | 0 | 0 | 0 | 0 |
| 16 | 33 | 97 | 78 | 0 | 0 | 0 | 0 |
| 17 | 0 | 48 | 37 | 0 | 0 | 0 | 0 |
| 18 | 46 | 102 | 96 | 0 | 0 | 16 | 0 |
| 19 | 12 | 53 | 26 | 0 | 0 | 0 | 0 |
| 20 | 69 | 137 | 107 | 0 | 0 | 0 | 0 |
| 21 | 0 | 26 | 20 | 0 | 0 | 0 | 0 |
| 22 | 60 | 162 | 110 | 0 | 0 | 0 | 0 |
| 25 | 0 | 18 | 7 | 0 | 0 | 0 | 0 |
| 26 | 0 | 7 | 9 | 0 | 0 | 0 | 0 |
| 29 | 0 | 5 | 0 | 0 | 0 | 0 | 0 |
| 30 | 0 | 68 | 0 | 0 | 0 | 0 | 0 |
| 31 | 0 | 0 | 4 | 0 | 0 | 0 | 0 |
| 32 | 0 | 8 | 0 | 0 | 0 | 0 | 0 |
| 33 | 0 | 15 | 0 | 0 | 0 | 8 | 0 |
| 34 | 0 | 8 | 0 | 0 | 0 | 0 | 0 |
| 35 | 0 | 0 | 9 | 0 | 0 | 0 | 0 |

A new double emulsion process has been developed for the manufacture of TIMP-GLIA particles. Based on the presented findings, the following conclusions are made.

Development Of Solubilization And Purification Procedures For Crude Gliadin Extracts From Wheat: Extraction of crude gliadin preparations using 70% ethanol allows a suitable alternative to TFA:DMSO to solubilize target gliadins. RP-HPLC in conjunction with LC-MS analysis demonstrated successful detection of alpha, beta, and gamma gliadin proteins species from 70% ethanol solubilized material.

Identification Of Appropriate Alternatives To Solubilize And Extract Gliadins From Purchased Crude Gliadins: Crude gliadin extracted with 70% ethanol yield material with higher gliadin content and reduced glutenin content, as compared to acetic acid extracts. LC-MS successfully detected α/β and γ gliadin proteins in material from two separate vendors.

Stress Testing Of Gliadin: Sonication did not significantly affect the RP-HPLC elution profile at 30 s (used in the double emulsion process). Stability of gliadin extracts was altered with increased temperature as demonstrated the RP-HPLC elution profile of gliadin. The effect of the lyophilization process for gliadin extracts significantly altered the RP-HPLC elution profile of gliadin from MP Biomedical but not Sigma-Aldrich. Mixing gliadin extracts with DMSO did not affect their RP-HPLC elution profile. However, the inclusion of DMSO in the sample injection broadened the solvent injection peak from 2-10 min. This should present minimal issues since protein quantification will be carried out using CBQCA assay. Based on these results, gliadin sourced from Sigma-Aldrich was acceptable.

Utilization Of A Double Emulsion Process In The Production Of TIMP-GLIA Particles: TIMP-GLIA particles were successfully fabricated using a double emulsion method using gliadin extracts processed with 70% ethanol. Heating of the 70% ethanol gliadin extract to 25-30° C. for 5-10 min was utilized to improve its solubility/clarity prior to particle fabrication. The concentration of gliadin measured in the 70% ethanol extract plays a determining role in the loading of TIMP-GLIA particles. A higher concentration results in higher measured gliadin loading.

Gliadin protein species could be detected from particles using SDS-PAGE and LC-MS.

TIMP-GLIA particles can be produced using the double emulsion process with controlled sizes (about 400 to about 800 nm), low zeta potentials (less than about −40 mV), low PDI (<less than about 0.3), controllable loadings (about 5 μg/mg to about 20 g/mg), and high encapsulation efficiencies.

Example 2a. Preparation of TIMP-GLIA Particles by the Double Emulsion Process

600 μL of gliadin in 70% ethanol (25 mg/mL) were added to 2 mL of 20% w/v poly(lactide-co-glycolide) in dichloromethane (200 mg/mL), and the mixture was sonicated for 30 seconds at 100% amplitude. After sonication, 10 mL of 1% w/v aqueous solution of poly(ethylene-all-maleic anhydride) was added to the mixture, and the resulted emulsion was sonicated for 30 seconds at 100% amplitude. The sonicated mixture was poured into 200 mL of 0.5% w/v poly(ethylene-alt-maleic anhydride) dissolved in water under stirring at 300 RPM. The particles were stirred for 10-14 hours to evaporate ethanol and dichloromethane.

Solutions of cryoprotectants can be prepared from mannitol and sucrose (sucrose 10 g/25 mL MilliQ water; mannitol 6 g/20 mL MilliQ water). The mannitol solution may require heating to dissolve (e.g., 70° C. for 15-30 min with frequent vortexing). Particle solution was passed through a 40 mm cell strainer. The solution was distributed into five 50 mL falcon tubes for a total volume of 40 mL in each tube. Particles were chilled on ice for 15 min and then centrifuged under a relative centrifugal force of 7000×g for 15 minutes at 4° C. Supernatant was aspirated completely. 3 mL of 0.1 M sodium bicarbonate-sodium carbonate buffer was added to each tube and the particles were chilled on ice for 15 min. The pellets were resuspended using a 1 mL pipette or a pipette aid equipped with a 5 mL serological pipette. 5 Tubes worth of particles were combined into two 50 mL conical tubes (resuspension of the particles could require harsh mixing; vortexing may not produce a homogenous particle suspension). After the pellets are dispersed well (no visible aggregates), 0.1 M sodium bicarbonate-sodium carbonate buffer was added to each tube until total volume was about 40 mL. The tubes were centrifuged under a relative centrifugal force of 7000×g for about 15 minutes at about 4° C., and the supernatant was aspirated completely. Another 3 mL of 0.1 M sodium bicarbonate-sodium carbonate buffer was added to each tube and the particles were chilled on ice for 15 min. The chilled particles were resuspended again, and 0.1 M sodium bicarbonate-sodium carbonate buffer was added to each tube until the total volume is 40 mL. The tubes were centrifuged under a relative centrifugal force of 7000×g for 15 minutes at 4° C., and the supernatant was aspirated completely.

3 mL of MilliQ water was added into each tube and the particles were chilled on ice for 15 min. The pellets were resuspended and additional MilliQ water was added until total volume was 12.5 mL to provide a homogeneous dispersion. The solution was passed through a 40 μm cell strainer, and used to prepare 15 tubes, 2 mL tubes for particle aliquoting. At least 3 of those tubes were pre-massed to determine the amount of particles per tube.

800 μL of the particle solution was pipetted into each tube and the remaining 0.5 mL of particle solution was saved for characterization by DLS/Zeta analysis in a 1.5 mL microcentrifuge tube (20 μL of particle sample in MilliQ water is used to perform DLS/Zeta analysis).

Out of 15 prepared tubes, 12 can receive cryoprotectant. For each tube that with cryoprotectant, 100 μL of the sucrose solution is mixed with 100 μL of the mannitol solution and added to the particles with mixing by pipette. The total volume per tube is 1 mL. The concentration of cryoprotectant is 4% w/v sucrose and 3% w/v mannitol.

All samples, including the ones with no cryoprotectant, except for the 0.5 mL sample saved for characterization, were frozen in the freezer at −80° C. for at least 5 hr. The samples were lyophilized for 20-50 hours to provide the TIMP-GLIA particles.

Samples are analyzed by size, zeta potential, polydispersity index (PDI), gliadin loading, encapsulation efficiency, SDS-PAGE, and mass spectrometry.

Example 2b. Determination of Antigen Concentration of TIMP-GLIA Particles and Purified Gliadin Extract Molecular Probes CBQCA Protein Quantitation Kit provides a rapid and highly sensitive method for the quantitation of proteins in solution. The kit utilizes the ATTO-TAG CBQCA reagent (3-(4-carboxybenzoyl)quinoline-2-carboxaldehyde) originally developed as a chromatographic derivatization reagent for amines. This reagent has also proven extremely useful for quantitating amines in solution, including the accessible amines in proteins. The ATTO-TAG CBQCA reagent is virtually non-fluorescent in aqueous solution; however, in the presence of cyanide, it reacts with primary amines such as those found in proteins to form highly fluorescent derivatives used to perform DLS/Zeta analysis).

Sample Preparation: TIMP-GLIA Particles: Dissolve 5-10 mg of TIMP-GLIA in DMSO to obtain a final concentration of 20 mg/mL. Purified gliadin extract: 70% ethanol extracted gliadin was diluted by 250-fold for the assay.

Prepare standard curve samples by serial dilution using gliadin interim standard as follows: 8000 ng (800 ug/mL), 4000 ng (400 ug/mL), 2000 ng (200 ug/mL), 1000 ng (100 ug/mL), 500 ng (50 ug/mL), 250 ng (25 ug/mL), 125 ng (12.5 ug/mL), 0 ng (0 ug/mL). Prepare a solution of purified gliadin extract in DMSO to use for the standard curve. (Note: mass 2 mg of purified gliadin extract and dissolve in 1 mL DMSO; 2 mg/mL). Using the solution prepared above, mix 400 μL of 2 mg/mL solution with 600 μL DMSO to achieve a concentration of 800 μg/mL. (Note: this is the highest concentration for the standard curve). Perform serial dilutions on the 800 μg/mL solution to obtain each concentration noted for the standard curve.

Perform the CBQCA assay: 125 uL of borate buffer pH 9.3 (described in CBQCA package insert) was added to each well of a black 96 well plate to be assayed. 10 uL of the standard curve samples, TIMP-GLIA samples, or 70% ethanol extracted gliadin samples were added to the wells containing borate buffer. For each sample, combine 10 uL of 5 mM CBQCA ATTO-Tag (Note: dilute the 40 mM stock solution) with 5 uL of 20 mM KCN (this is the stock solution). 15 uL of the assay reagent from step 5 was added to each well to be assayed. The plate was read at 465 nm excitation and 550 nm emission.

Measurement of the purified gliadin extract concentration: The concentration of the extract will be calculated by comparing the measured fluorescence intensity of the extract to the standard curve of purified gliadin extract.

Measurement of the gliadin content in TIMP-GLIA: The concentration of gliadin encapsulated in TIMP-GLIA will be calculated by comparing the measured fluorescence intensity of the extract to the standard curve of purified gliadin extract. The loading of gliadin within TIMP-GLIA is defined as: micrograms of gliadin determined by CBQCA assay per milligram of TIMP-GLIA×100. (Note: 200 μg of TIMP-GLIA is added to the CBQCA assay per well).

In some embodiments, purified gliadin extract concentration by CBQCA should be greater than 25 mg/mL. In some embodiments, the average loading value for TIMP-GLIA should be between 10 μg/mg and 20 μg/mg.

Example 2c. Determination of Zeta Potential of TIMP-GLIA Particles

Laser Doppler Micro-electrophoresis is used to measure zeta potential. An electric field is applied to a solution of molecules or a dispersion of particles, which then move with a velocity related to their zeta potential. This velocity is measured using a patented laser interferometric technique called M3-PALS (Phase analysis Light Scattering). This enables the calculation of electrophoretic mobility and from this the zeta potential and zeta potential distribution.

Resuspend 250 μg of particles in 1 mL of 18.2 MΩ water (e.g., MilliQ water or similar) in a 1.5 mL microcentrifuge tube. Transfer the particle suspension carefully into a disposable folded capillary cell (e.g., Malvern cat #: DTS1070) avoiding the introduction of any bubbles. Insert the cuvette with the particle suspension into the cuvette holder of the ZetaSizer Nano ZSP (Malvern Zetasizer Nano ZS or ZSP. Use the following settings in the DTS Nano software: Measurement type: Zeta potential: Material: Polystyrene latex; Refractive index: 1.330; Absorption: 0.010; Medium: Water; Temperature: 25° C.; Viscosity: 0.8872 cP; Dielectric constant: 78.5; Smoluchowski parameters; Measurement: Automatic duration).

Average the measured values for 3 measurements to obtain the zeta potential and associated standard deviation.

Particle average zeta potential between −40 to −80 mV.

Example 2d. Determination of Particle Diameter of TIMP-GLIA Particles

Dynamic Light Scattering (DLS) is used to measure particle and molecule size. DLS measures the diffusion of particles moving under Brownian motion, and converts this to size and a size distribution using the Stokes-Einstein relationship. Non-Invasive Back Scatter technology (NIBS)

is incorporated to give the highest sensitivity simultaneously with the highest size and concentration range.

Resuspend 250 µg of particles in 1 mL of 18.2 MΩ water (e.g., MilliQ water or similar) in a 1.5 mL microcentrifuge tube. Transfer the particle suspension carefully into a sizing cuvette (12 mm square polystyrene cuvettes (Fisher: NC9430276; Sarstedt Inc. CUVETTE SQ 4 Side 4ML RPK/PK100)) avoiding the introduction of any bubbles. Insert the cuvette with the particle suspension into the cuvette holder of the ZetaSizer Nano ZSP (Malvern Zetasizer Nano ZS or ZSP. Use the following settings in the DTS Nano software: Measurement type: Size; Material: Polystyrene latex; Refractive index: 1.590; Absorption: 0.010; Medium: Water; Temperature: 25° C.; Viscosity: 0.8872 cP; Refractive index: 1.330; Measurement: 1730 backscatter, automatic duration).

Average the measured values for 3 measurements to obtain the z-average size, polydispersity index (PDI), and associated standard deviation.

Z-average particle size of TIMP-GLIA between 400-800 nm. PDI<0.3. Data quality result from auto-generated report by instrument software reads 'good'.

The invention claimed is:

1. A method for preparing a pharmaceutical composition comprising Toleragenic Immune Modifying nanoparticles-containing Gliadin (TIMP-GLIA) particles, the method comprising:
    (a) homogenizing gliadin dissolved in an aqueous media with an oil phase comprising a polymer to produce water-in-oil primary emulsion particles, wherein the aqueous media comprises ethanol or acetic acid;
    (b) mixing the primary emulsion particles with a surfactant;
    (c) homogenizing the mixture of (b) to provide secondary emulsion particles; and
    (d) hardening the secondary emulsion particles,
    wherein the hardened secondary emulsion particles have a zeta potential of about −80 to about −30 mV.

2. The method of claim 1, wherein hardening the secondary emulsion particles comprises evaporation of the oil phase.

3. The method of claim 1, wherein the aqueous media is 70% ethanol.

4. The method of claim 1, wherein the gliadin concentration in the aqueous media is greater than about 25 mg/mL.

5. The method of claim 1, wherein the polymer is poly(lactide-co-glycolide).

6. The method of claim 1, wherein the surfactant is poly(ethylene-a/t-maleic anhydride).

7. The method of claim 1, further comprising:
    processing the secondary emulsion particles such that the average particle size of the hardened secondary emulsion particles is between about 400 nm and about 800 nm.

8. The method of claim 1, wherein hardened secondary emulsion particles have a zeta potential of about −80 to about −40 mV.

9. The method of claim 1, wherein the hardened secondary emulsion particles are free from trifluoroacetic acid.

10. The method of claim 1, wherein the hardened secondary emulsion particles have an antigen load of about 10 to about 20 µg/mg of the polymer.

11. A process for the preparation of a pharmaceutical composition comprising Toleragenic Immune Modifying nanoparticles-containing Gliadin (TIMP-GLIA) particles, said process comprising the steps of:
    a) producing primary water-in-oil emulsion particles by homogenization of gliadin dissolved in an aqueous media comprising ethanol or acetic acid in an oil phase comprising polymer;
    b) adding an emulsifier to the primary emulsion particles; and
    c) homogenizing the mixture of step b) to provide secondary water-in-oil-in-water emulsion particles.

12. The process of claim 11 wherein gliadin is purified by extraction from crude gliadin from wheat with an extraction solvent of ethanol or acetic acid.

13. The process of claim 12, wherein the extraction solvent is 70% ethanol.

14. The process of claim 12, wherein the gliadin concentration in the extraction solvent is greater than 25 mg/mL.

15. The process of claim 11 further comprising the steps of:
    d) hardening the secondary emulsion particles;
    e) centrifuging the hardened secondary emulsion particles; and
    f) freeze drying the secondary emulsion particles.

16. The process of claim 11 wherein the polymer is a biodegradable polymer.

17. The process of claim 11 wherein the polymer is poly(lactide-co-glycolide).

18. The process of claim 11 wherein the emulsifier is selected from the group consisting of polyethylene glycol (PEG), polyoxyethylene (20) sorbitan monooleate, gelatin, dextran, pluronic L-63, polyvinyl alcohol (PVA), methylcellulose, lecithin, DMAB (didodecyldimethylammonium bromide), poly(ethylene-a/t-maleic anhydride), and vitamin E TPGS (D-a-tocopheryl polyethylene glycol 1000 succinate).

19. The process of claim 18 wherein the emulsifier is poly(ethylene-a/t-maleic anhydride).

20. The process of claim 11, wherein the TIMP-GLIA particles have a particle size of about 400 to about 800 nm.

21. The process of claim 11, wherein the TIMP-GLIA particles have an antigen load of about 10 to about 20 µg/mg of PLGA.

22. The process of claim 11, wherein the TIMP-GLIA particles have a zeta potential of about −80 to about −40 mV.

23. The process of claim 11 wherein the emulsifier comprises one or more of polyethylene glycol (PEG), polyoxyethylene (20) sorbitan monooleate, gelatin, dextran, pluronic L-63, polyvinyl alcohol (PVA), methylcellulose, lecithin, DMAB (didodecyldimethylammonium bromide), poly(ethylene-alt-maleic anhydride), and/or vitamin E TPGS (D-a-tocopheryl polyethylene glycol 1000 succinate).

24. The method of claim 1, wherein the aqueous media comprises acetic acid.

25. The method of claim 1, wherein the hardened secondary emulsion particles have a zeta potential of about −50 to about −40 mV.

26. The process of claim 12, wherein the extraction solvent is acetic acid.

27. The process of claim 11, wherein the TIMP-GLIA particles have a zeta potential of about −50 to about −40 mV.

* * * * *